United States Patent [19]

Jewell

[11] Patent Number: 5,556,976
[45] Date of Patent: Sep. 17, 1996

[54] REACTIVE CYCLIC N-SULFATOIMIDES AND CELLULOSE CROSSLINKED WITH THE IMIDES

[76] Inventor: Richard A. Jewell, 5215 146th Ave. SE., Bellevue, Wash. 98006

[21] Appl. No.: 235,723

[22] Filed: Apr. 29, 1994

Related U.S. Application Data

[63] Continuation of Ser. No. 820,333, Jan. 13, 1992, Pat. No. 5,366,591, which is a continuation-in-part of Ser. No. 665,761, Mar. 7, 1991, Pat. No. 5,252,275, and a continuation-in-part of Ser. No. 607,268, Oct. 31, 1990, abandoned, which is a continuation-in-part of Ser. No. 395,208, Aug. 17, 1989, Pat. No. 5,225,047, which is a continuation-in-part of Ser. No. 284,885, Dec. 15, 1988, abandoned, which is a continuation-in-part of Ser. No. 140,922, Dec. 28, 1987, abandoned, which is a continuation-in-part of Ser. No. 4,729, Jan. 20, 1987, abandoned.

[51] Int. Cl.$^6$ .................................................. C07D 403/04
[52] U.S. Cl. ........................ 544/296; 544/314; 548/520; 548/542
[58] Field of Search ................................ 548/520, 542; 544/296, 314

[56] References Cited

U.S. PATENT DOCUMENTS

| | | | |
|---|---|---|---|
| 3,208,676 | 9/1965 | Jensen | 241/195 |
| 3,224,926 | 12/1965 | Bernardin | 162/146 |
| 3,395,708 | 8/1968 | Hervey et al. | 128/284 |
| 3,440,135 | 4/1969 | Chung | 162/157 |
| 3,482,788 | 12/1969 | Newell | 241/69 |
| 3,519,211 | 7/1970 | Sakulich et al. | 241/18 |
| 3,554,862 | 1/1971 | Hervey et al. | 162/158 |
| 3,637,146 | 1/1972 | Banks | 241/194 |
| 3,658,613 | 4/1972 | Steiger | 156/153 |
| 3,677,886 | 7/1972 | Forssblad et al. | 162/72 |
| 3,750,962 | 8/1973 | Morgan, Jr. | 241/18 |
| 3,765,971 | 10/1973 | Fleissner | 156/62.2 |
| 3,819,470 | 6/1974 | Shaw et al. | 162/157 C |
| 3,825,194 | 7/1974 | Buell | 241/191 |
| 3,901,236 | 8/1975 | Assarsson et al. | 128/284 |
| 3,950,218 | 4/1976 | Levesque | 162/201 |
| 3,950,219 | 4/1976 | Levesque | 162/201 |
| 3,966,126 | 6/1976 | Werner | 241/18 |
| 3,987,968 | 10/1976 | Moore et al. | 241/28 |
| 4,144,122 | 3/1979 | Emanuelsson et al. | 162/158 |
| 4,241,881 | 12/1980 | Laumer | 241/28 |
| 4,252,279 | 2/1981 | Johansson et al. | 241/27 |
| 4,303,471 | 12/1981 | Laursen | 162/158 |
| 4,332,586 | 6/1982 | North | 8/186 |
| 4,351,699 | 9/1982 | Osborn, III | 162/112 |
| 4,406,415 | 9/1983 | Greer | 241/194 |
| 4,476,323 | 10/1984 | Hellsten et al. | 564/294 |
| 4,533,507 | 8/1985 | Tao | 261/153 |
| 4,572,440 | 2/1986 | Tao | 241/23 |
| 4,600,462 | 7/1986 | Watt | 156/278 |
| 4,650,127 | 3/1987 | Radwanski et al. | 241/28 |
| 4,729,516 | 3/1988 | Williams, Jr. | 241/186.4 |
| 4,822,453 | 4/1989 | Dean et al. | 162/157.6 |
| 4,853,086 | 8/1989 | Graef | 162/157.6 |
| 4,889,595 | 12/1989 | Herron et al. | 162/157.6 |
| 4,913,773 | 4/1990 | Knudsen et al. | 162/129 |
| 4,935,022 | 6/1990 | Lash et al. | 604/368 |
| 5,217,445 | 6/1993 | Young et al. | 604/381 |

FOREIGN PATENT DOCUMENTS

| | | |
|---|---|---|
| 118498 | 3/1984 | European Pat. Off. . |
| 0225940 | 6/1987 | European Pat. Off. . |
| 0399564 | 11/1990 | European Pat. Off. . |
| 0440472A1 | 8/1991 | European Pat. Off. . |
| 2255414 | 12/1974 | France . |
| 2902257A | 7/1980 | Germany . |
| 159-148 | 5/1981 | Germany . |
| 93769 | 1/1955 | Norway . |
| 950-432 | 8/1982 | U.S.S.R. . |
| WO84/00904 | 9/1983 | WIPO . |

OTHER PUBLICATIONS

American Society of Agricultural Engineers, ASAE publication 10–81, *Forest Regeneration*, 1080117, (Mar. 1981). pp. 108–117.

VanVerst et al., *Amine-Induced Lossen Rearrangments of 3-Hydroxy-5, 6-dihrodouracil and N-Hydroxysuccinimide Benzenesulfonates*, Journal of Heterocyclic Chemistry, vol. 16 (1979) p. 1329.

HBA, Weyerhaeuser Paper Company, 1990.

Primary Examiner—Jacqueline Haley

[57] ABSTRACT

A method of forming a crosslinked cellulose product is disclosed wherein cellulose fibers are exposed to a solution that includes a catalyst and a crosslinking agent selected from the group consisting of a cyclic N-sulfatoimide or cyclic N-phosphatoimide; a dimethoxyethanal; a mixture of glyoxal and imidazolidone; a diethanol; or a periodate. Specific examples of the crosslinking agents of the present invention include pyridinium N-sulfatosuccinimide; 2,2'-sulfonyldiethanol; sodium periodate; a mixture of dimethoxyethanal and urea; and a mixture of glyoxal and 2-imidazolidone. An acid or base catalyst, as appropriate, may be used with the crosslinking agent to increase the crosslinking reaction rate. In especially preferred embodiments, cellulose fibers are exposed to the crosslinking agent and catalyst, then separated into individualized fibers in a fiberizer. The individualized fibers are then dried and cured at an elevated temperature such that intrafiber cellulose crosslinking bonds are formed to the substantial exclusion of interfiber bonds. The resulting cellulose fibers have high absorbency, bulk, and wet and dry resiliency that makes them suitable for use in such cellulose products as paper towels, diapers, and sanitary products.

2 Claims, 7 Drawing Sheets

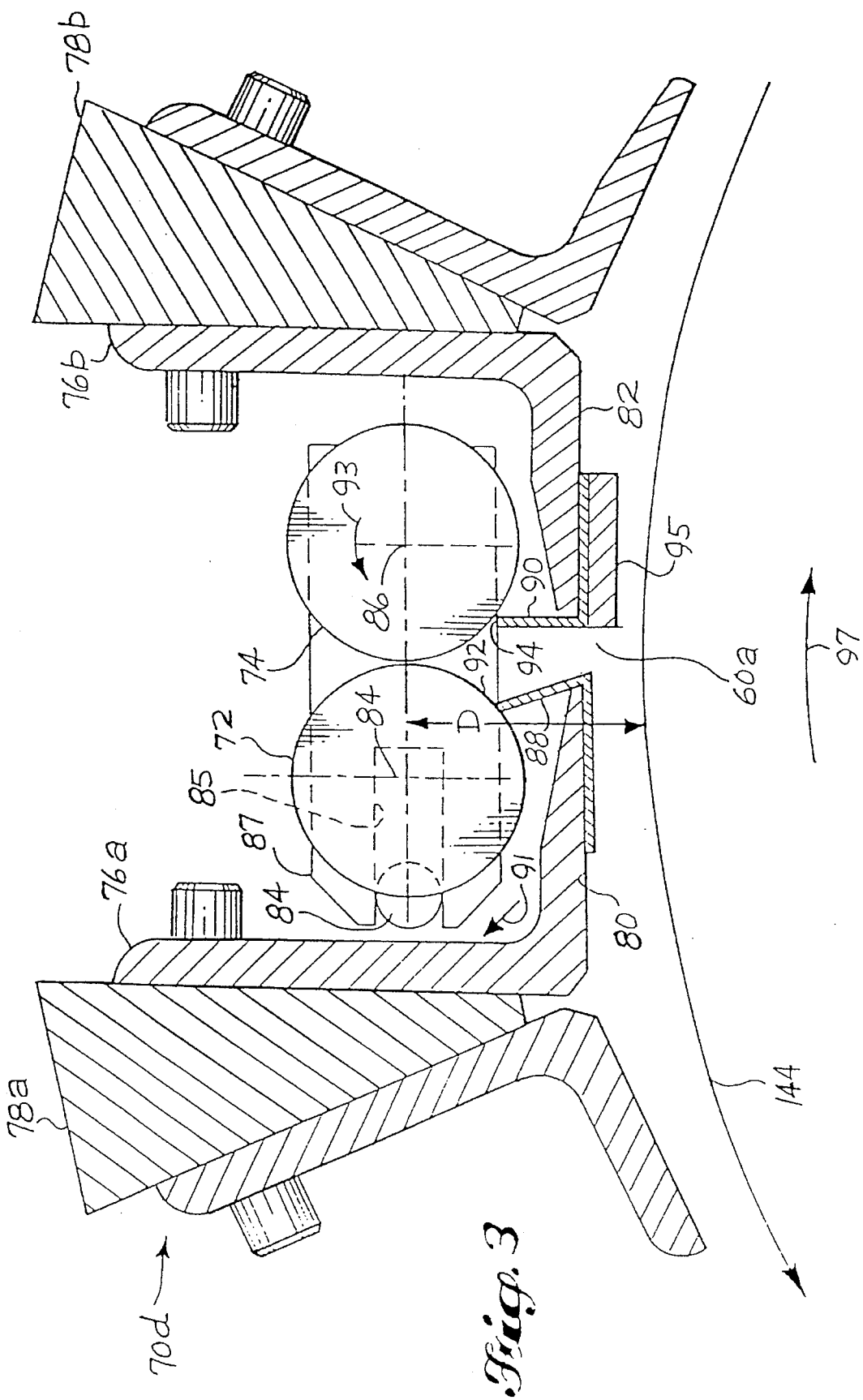

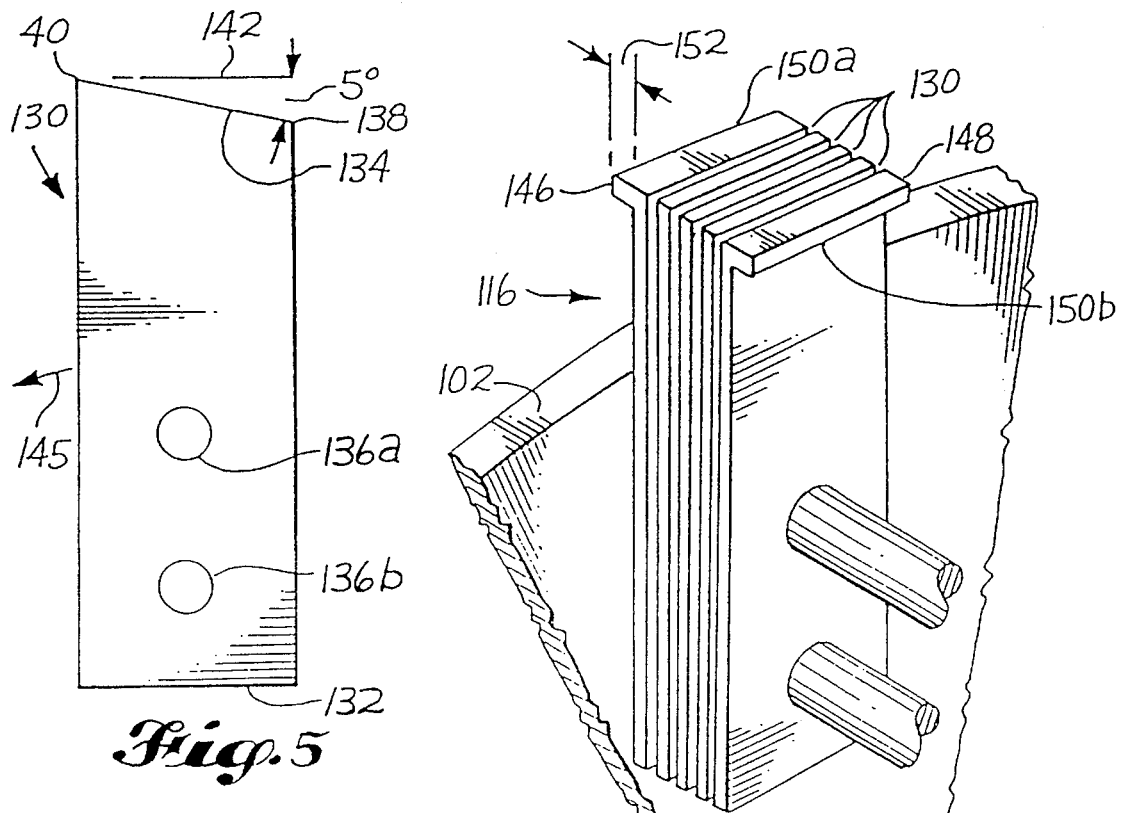
Fig. 5
Fig. 6
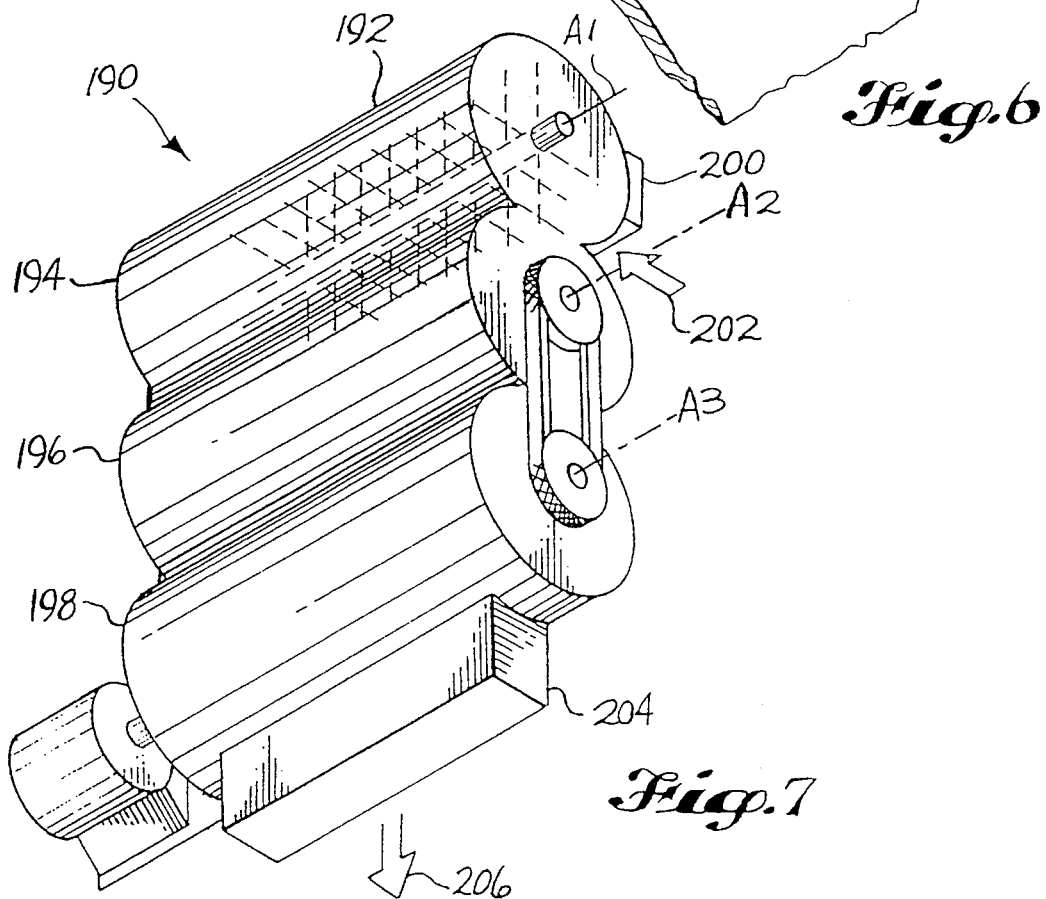
Fig. 7

REACTIVE CYCLIC N-SULFATOIMIDES AND CELLULOSE CROSSLINKED WITH THE IMIDES

CROSS-REFERENCE TO RELATED CASES

This is a continuation of application Ser. No. 820,333, filed Jan. 13, 1992, and now U.S. Pat. No. 5,366,591, which, in turn, was a continuation-in-part of application Ser. No. 07/665,761, filed Mar. 7, 1991, U.S. Pat. No. 5,253,275; and Ser. No. 07/607,268, filed Oct. 31, 1990, abandoned, which is a continuation-in-part of Ser. No. 07/395,208, filed Aug. 17, 1989, U.S. Pat. No. 5,225,047, which is a continuation-in-part of Ser. No. 07/284,885, filed Dec. 15, 1988, now abandoned; which is a continuation-in-part of Ser. No. 07/140,922, filed Dec. 28, 1987, now abandoned; which is a continuation-in-part of Ser. No. 07/004,729, filed Jan. 20, 1987, now abandoned.

BACKGROUND OF THE INVENTION

1. Field of the Invention

This invention relates to a method of making intrafiber crosslinked cellulose and the product resulting from the process. The invention is especially directed to a crosslinked cellulose having a high wet and dry resilience, high bulk, and superior absorbency.

2. General Discussion of the Background

It is known in the art that resilient bulking fibers are useful for the preparation of bulky and more absorbent paper structures. Such paper structures are useful for the manufacture of products such as handsheets, towels, tissues, filters, paperboard, diapers, sanitary napkins, hospital dressings and the like. Crosslinked cellulose materials may be generated by reacting cellulose fibers with crosslinking agents which are capable of combining with at least two hydroxyl groups within a single cellulose molecule, or between adjacent cellulose molecules. The crosslinking agent must be difunctional such that it will react with at least two of the hydroxyl groups in the cellulose molecule to form the crosslink.

One method for obtaining resilient bulking fibers is by crosslinking cellulose fibers by treatment with a chemical compound. U.S. Pat. No. 3,819,470 discloses cellulosic fibers having a substantive polymeric compound reacted with and attached to the fibers. The modified fibers are characterized by reduced swellability and a reduced capability of natural fiber-to-fiber bonding when compared to unmodified cellulosic fibers. U.S. Pat. No. 4,431,481 discloses modified cellulosic fibers produced by treating the fibers with copolymers of maleamic acid. Other known techniques include treatment of fibers with cationic urea formaldehyde resins, (U.S. Pat. No. 3,756,913), methylol ureas and melamines (U.S. Pat. No. 3,440,135), formaldehyde (U.S. Pat. No. 3,224,926), with the condensation product of acrolein and formaldehyde, (U.S. Pat. No. 3,183,054), bis-acrylamides (Eur. Patent No. 213,415), and treatment with glyoxal or glutaric dialdehyde (WO 88104704, U.S. Pat. No. 4,822,453, and U.S. Pat. No. 4,853,086). Copending U.S. patent application Ser. No. 07/607,268 discloses a crosslinking process in which the crosslinking agent is dimethyldihydroxy-ethylene urea (DMDEU).

A drawback of many of these prior crosslinking agents is that they are inefficient crosslinkers or are toxic. The problem of toxicity is a particular concern with formaldehyde crosslinkers. Formaldehyde is toxic when inhaled, and can be strongly irritating to the skin and mucus membranes. Concerns have also been expressed that formaldehyde is teratogenic and carcinogenic. Public anxieties about environmental safety and occupational hazards have provided a special impetus to find new, non-formaldehyde crosslinkers.

Three techniques have generally been used to produce intrafiber crosslinked material. They are dry crosslinking, aqueous crosslinking, and crosslinking in a non-aqueous solution. In the dry crosslinking process, the cellulose fibers are crosslinked while in an unswollen, collapsed state. Dry crosslinked fibers are stiffened by crosslink bonds, such that absorbent structures made from the fibers have high wet and dry resilience, and low fluid retention. Aqueous solution crosslinked fibers are produced by crosslinking fibers in an aqueous solution, such that the swelling effect of water causing the fibers to be crosslinked in a swollen condition. Compared to dry crosslinked fibers, aqueous crosslinked fibers have increased flexibility, reduced stiffness, higher fluid retention, and lower wet and dry resilience. Nonaqueous crosslinking occurs when individualized, dehydrated, nonswollen fibers are contacted with a crosslinking agent in a substantially nonaqueous solution. The resulting fibers are stiff and exhibit high wet and dry resilience.

An example of using dry crosslinking technology is U.S. Pat. No. 3,440,135 to Chung. This patent discloses a technique of pre-soaking cellulose fibers in an aqueous solution of a crosslinking agent to reduce interfiber bonding. The treated fibers are then aged prior to carrying out a drying stage, in which the fibers are heated to effect crosslinking. The Chung patent suffers from the drawback that the wet fiber mat must be stored between 16 and 48 hours, in order to minimize nit formation resulting from incomplete difiberization.

Another example of dry crosslinking technology is U.S. Pat. No. 3,224,926 to Bernardin. That patent describes treating cellulosic material with a crosslinking agent such as formaldehyde or dimethylolurea. Individualized, crosslinked fibers are produced by impregnating swollen fibers in an aqueous solution with a crosslinking agent, dewatering and then mechanically defiberizing the fibers, and then drying the fibers at an elevated temperature to crosslink the fibers while they are substantially individualized. The fibers are crosslinked in an unswollen, collapsed state as a result of being dehydrated prior to crosslinking. The products made by this dry crosslinking process exhibit high absorbency and high wet and dry resilience.

An example of an aqueous crosslinking process is U.S. Pat. No. 3,241,533 to Steiger, in which the cellulose fibers are crosslinked in an aqueous solution with a crosslinking agent and a catalyst. The product made from this process was said to exhibit high fluid retention and great flexibility compared to a product made from a dry crosslinking process. Finally, an example of a nonaqueous crosslinking process is U.S. Pat. No. 4,035,147 to Sangenis et al. In this process, the lack of water present in the solution keeps the cellulose fibers in a state similar to that in the dry crosslinking process. While in the nonaqueous solution, the cellulose fibers are crosslinked with a crosslinking agent and a catalyst. Like dry crosslinked fibers, the nonaqueous crosslinked fibers are very stiffened by crosslink bonds, and absorbent materials made from these fibers have high wet and dry resilience.

Various devices are known in the art for treating fibers with crosslinking agents in mat form and thereafter breaking the mats into individual fibers. For example, U.S. Pat. No. 3,440,135 to Chung discloses a mechanism for applying a crosslinking agent to a cellulosic fiber mat. The mat is then aged and passed (while still wet) through a fiberizer, such as a hammermill to fiberize the mat. The resulting loose fibers are then dried in a two stage dryer. The first dryer stage is at a temperature sufficient to flash water vapor from the fibers and the second dryer stage is at a temperature that cures the crosslinking agent. A cyclone separator then separates the fibers from the gas for subsequent collection. The Chung apparatus suffers from the drawback of requiring the inconvenient and costly storage of wet fiber mats (e.g. in roll form) for a substantial period of time in order to minimize nit formation.

Unfortunately, fiberization processes known in the art which employ currently available fiberizing or comminution machinery yield crosslinked fibers that have too many nits and knots to be acceptable for many uses. A probable reason is that such machinery has excess dead space where fibers are excessively pressed together and/or has localized regions of elevated temperature hot enough to cause premature curing of the crosslinking agent while fibers are in intimate contact with each other. Since fiberization is performed on a mat that is still wet with the uncured crosslinking agent, dead spaces and hot spots in the fiberizer would encourage the formation of interfiber bonds, which form nits, that virtually cannot be broken by downstream equipment.

Interfiber bonding in a conventional fiberizer apparatus can also lead to production of excessive amounts of "fines," which are undesirably short fibers due principally to fiber breakage. Crosslinking imparts substantial brittleness to cellulose fibers, which thereby exhibit limited compliance to mechanical stresses. Nits are especially susceptible to mechanical stresses because of their density which is much greater than the density of individual fibers. Excess fiber breakage and fines not only degrade absorbency but can substantially reduce the loft and resiliency of a product made from crosslinked fibers.

Hence there is a need for a process of producing a product made of individualized crosslinked cellulose fibers that have minimal nits and knots. It is therefore an object of the invention to produce treated fibers, such as intrafiber crosslinked cellulose, having a nit level lower than levels obtainable with existing equipment. There is also a need for such an apparatus that will produce fibers from a mat comprised of crosslinked cellulose while not causing significant breakage of individual fibers of the mat.

It is yet another object to provide crosslinking agents that are less toxic and provide a product having high wet and dry resilience, high bulk, and superior absorbance.

Finally, it is an object to provide a crosslinking process that operates at a pH that is compatible with standard unmodified papermaking equipment.

These and other objects of the invention will be understood more clearly by reference to the following detailed description and drawings.

SUMMARY OF THE INVENTION

The foregoing objects are achieved by providing a method of forming an intrafiber crosslinked cellulose product in which cellulose fibers or individualized cellulose fibers are exposed to an aqueous solution comprising a catalyst and a crosslinking agent selected from the group consisting of cyclic N-sulfatoimide; a mixture of glyoxal and imidazolidone; a periodate or salt thereof; dimethoxyethanal and $OH-R_1-R_2-R_1-OH$ wherein $R_1$ is ethyl and $R_2$ is sulfonyl or

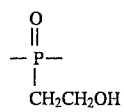

The catalyst and crosslinking agent are exposed to the cellulose fiber in a sufficient amount for a sufficient period of time at a sufficient temperature to crosslink molecules of cellulose in the fibers. The crosslinking agent can be used to crosslink various cellulose products, such as liner board, wood, and individualized cellulose fibers for absorbent products such as paper towels, diapers, and sanitary products.

In some specific embodiments, the method further comprises the step of individualizing the cellulose fibers before crosslinking the molecules of cellulose in the fibers. The fibers are exposed to the crosslinking agent and catalyst by spraying them on a mat of cellulose fibers at a fiber treatment zone, then conveying the mat through the fiber treatment zone directly into a fiberizer without stopping to cure the crosslinking substance. The fibers are then separated in a fiberizer by hammering them into substantially unbroken individual cellulose fibers, and then drying and curing the individual cellulose fibers. The fiberizer of the present invention individualizes fibers such that they have a nit level of no more than about 3 after individualization in the fiberizer.

The cyclic N-sulfatoimide crosslinker preferably comprises:

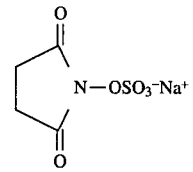

I

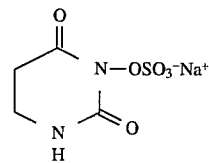

II

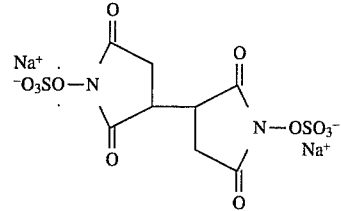

III

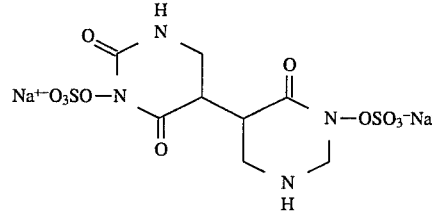

IV or N-sulfatophthalimide, but is most preferably an N-sulfatosuccinimide salt.

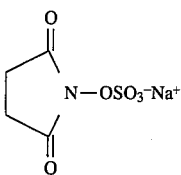

A basic catalyst is used with the N-sulfatoimide, preferably sodium hydroxide in an amount of 1–25% by weight of the treated cellulose, preferably 10% by weight. The sulfatoimide crosslinking agent is preferably present in an amount of 1–20% by weight, more preferably 5–10%, most preferably 10% by weight.

In yet other embodiments, the crosslinking agent is sulfonyldiethanol and the catalyst is a basic catalyst. The sulfonyldiethanol crosslinking agent is preferably present in an amount of 10% by weight of the treated product. The ratio by weight of crosslinker to catalyst is preferably about 5:1. In especially preferred embodiments the catalyst is NaOH, and is preferably present in an amount of 1–2% by weight.

In another embodiment, the crosslinker is glyoxal and 2-imidazolidone in the presence of an acidic catalyst. The glyoxal and imidazolidone are preferably present in a molar ratio of 1:1 to 3:1, more preferably 2:1. The glyoxal is preferably present in an amount of 1–5% by weight, while 1–4% of the imidazolidone is used.

When the crosslinking agent is sodium periodate, the catalyst should be an acidic catalyst, preferably one that lowers the pH to less than 5, and most preferably to the range of 2–5. An especially preferred catalyst is alum or $Al_2(SO_4)_3$.

In those embodiments wherein the crosslinking agent is dimethoxyethanal, the dimethoxyethanal may optionally be combined with an imidazolidone, for example 2-imidazolidone, wherein the dimethoxyethanal and imidazolidone are present in a molar ratio of 1:1 to 3:1, preferably 2:1. The dimethoxyethanal can also be combined with a urea compound, such as N-N' dimethylurea, preferably in a 2:1 molar ratio. An acid catalyst is used to catalyze the dimethoxyethanal crosslinking reaction. The dimethoxyethanol is preferably present in an amount of 2–14% by weight of the treated cellulose product, preferably 9% by weight.

The present invention also includes crosslinking compounds selected from the group consisting of Compounds I–IV above.

The invention also includes compositions comprising a mixture of glyoxal and imidazolidone, preferably in a molar ratio of 1:1 to 3:1, more preferably 2:1. An acid catalyst may be present in the composition. In other embodiments, the invention further includes cellulose products produced by the crosslinking method of the present invention.

The present method is preferably used to prepare a quantity of individual crosslinked cellulose fibers from one or more mats comprising non-crosslinked cellulose fibers. The method is preferably performed with an apparatus that includes an applicator which applies a crosslinking substance to a mat of cellulose fibers at a fiber treatment zone; a fiberizer having a fiberizer inlet; and a conveyor that conveys the mat through the fiber treatment zone and directly to the fiberizer inlet without stopping for curing. The fiberizer provides sufficient hammering force to separate the cellulose fibers of the mat into a fiber output of substantially unbroken individual cellulose fibers. A dryer coupled to the fiberizer receives the fiber output, dries the fiber output, and cures the crosslinking substance, thereby forming dried and cured fibers. The fiberizer preferably fiberizes the treated mat to form a fiber output having a low nit level, such as a nit level of no more than about 3.

Representative conveyors include, but are not limited to, conveyor belts and roller mechanisms. In the fiber treatment zone, the crosslinking substance can be applied to the mat via any suitable means including, but not limited to, spraying, roller coating, and a combination of spraying and roller coating. The applicator that applies the crosslinking agent is preferably a shower spray and a subsequent impregnation roller that presses the crosslinking substance into the mat. In especially preferred embodiments, the shower spray includes a pair of opposing shower spray applicators that direct droplets of the crosslinking agent toward each face of the mat.

The dryer of the apparatus preferably includes a drying zone for forming dried fibers, and a curing zone for curing the crosslinking substances on the dried fibers. The drying zone preferably includes the expansion chamber, which has an inlet for receiving the individual cellulose fibers from the restricted diameter conduit. The dryer inlet has a temperature within the range of about 200°–315° C. so as to flash evaporate moisture from and expand the cellulose fibers. The subsequent curing zone has an outlet through which the dried and cured fibers are delivered from the dryer. The outlet of the curing zone preferably has a temperature within a range of about 140°–180° C.

The fiberizer apparatus comprises at least an attrition device which produces a low nit level fiber output. The fiberizer may also optionally include a disk refiner of conventional design coupled to the attrition device and a fluff generator of novel design coupled to the disk refiner.

The present invention also includes a method of producing crosslinked cellulose fibers by applying one of the crosslinking substances of the present invention to a mat of cellulose fibers at a fiber treatment zone, then conveying the mat from the fiber treatment zone directly into a fiberizer without stopping to cure the crosslinking substance. The fiberizer separates the fibers by hammering them into substantially unbroken individual cellulose fibers, preferably having a nit level of no more than about 3. The separated fibers are then dried at a temperature of about 200°–315° C. so as to flash evaporate water from the fiber output, and then cured at a temperature of about 140°–180° C.

BRIEF DESCRIPTION OF THE DRAWINGS

FIG. 3 is a transverse sectional view of a mat feeder assembly of the preferred embodiment of the attrition device.

FIG. 5 is a plan view of a hammer plate used in the rotor of FIG. 4.

FIG. 6 is an isometric view of a stack of hammer plates used in the rotor of FIG. 4.

FIG. 7 is an isometric view of the exterior of a preferred embodiment of a fluff generator included as an option in the apparatus of the present invention.

DETAILED DESCRIPTION

Figure 1:
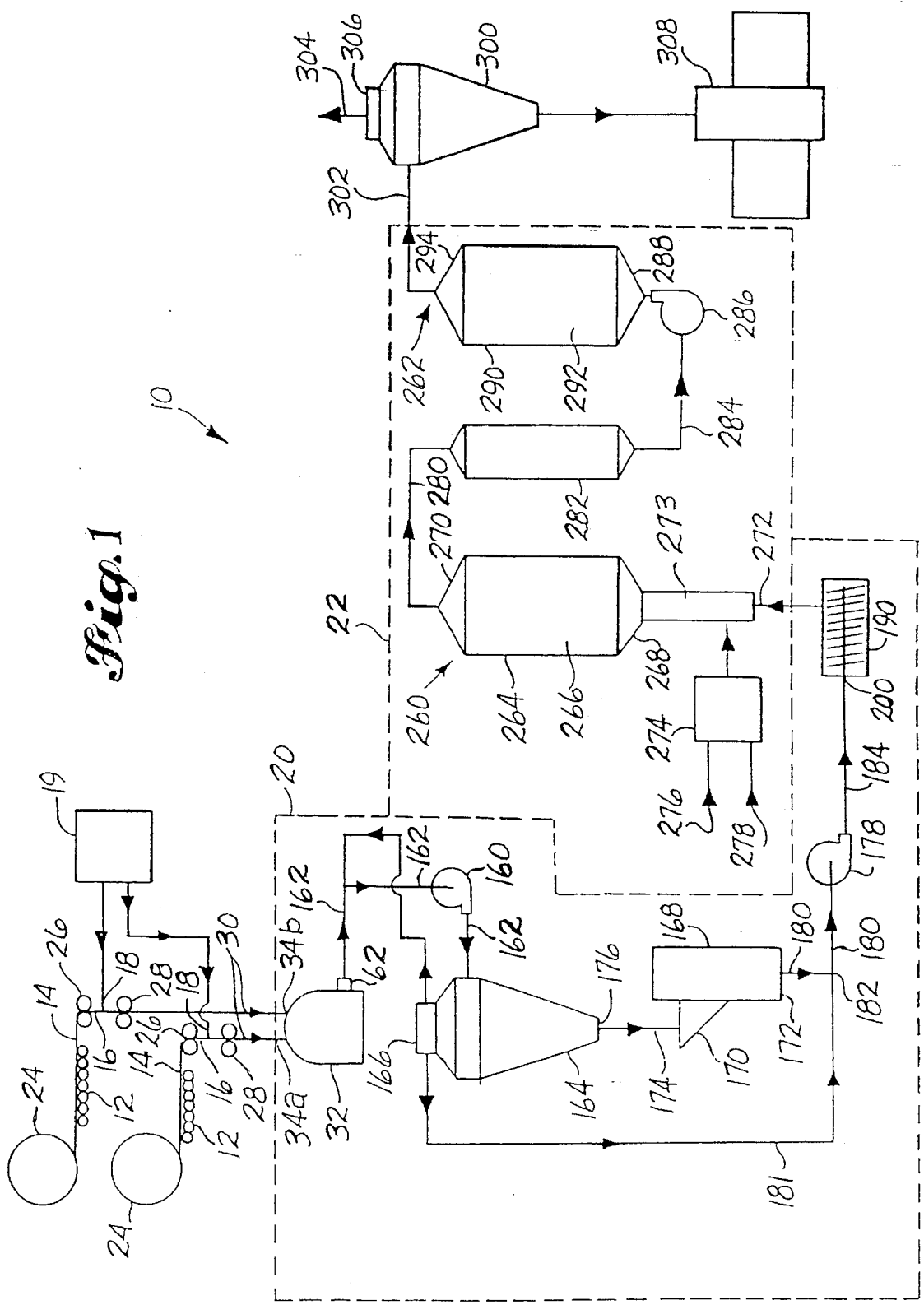
FIG. 1 is a schematic depiction of the components of one embodiment of the apparatus of the present invention that is used to individualize and crosslink cellulose fibers.

The use of the crosslinking agents of the present invention are illustrated in the following examples.

EXAMPLE I

N-sulfatosuccinimide Crosslinker

This example shows the effect of using N-sulfatosuccinimide as a crosslinking agent. The N-sulfatosuccinimide was prepared by combining 11.5 g of N-hydroxysuccinimide and 15.8 g of pyridine in 150 ml of dichloromethane. To this solution, 11.7 g of chlorosulfonic acid was added over a 20-minute period with cooling to maintain the temperature at 5°–15° C. The solution was stirred at room temperature for about 16 hours, then suction filtered, and the solid precipitate washed with three 100 ml portions of dichloromethane to remove pyridine hydrochloride. The resulting colorless solid was then dried to yield approximately 22.5 g of pyridinium N-sulfatosuccinimide.

The crosslinking of the cellulose with pyridinium N-sulfatosuccinimide was carried out by dissolving 1.6 g of pyridinium N-sulfatosuccinimide and 1.0 g of sodium bicarbonate catalyst in 10 ml of water. The solution was washed twice with dichloromethane in a separatory funnel to remove pyridine, and the water phase was diluted to 15.5 ml with water and immediately distributed dropwise over the surface of a 15.5 g piece of pulpsheet made from NF105 pulp available from the Weyerhauser Company of Federal Way, Wash. The pulpsheet was made from 2:1 of NF105:Buckeye pulp. The wet pulp was placed in a plastic bag and pressure rolled to evenly distribute the liquid. The pulpsheet was then converted to fluff by passing it twice through a pin mill fluffer, and the fluff was cured in an oven at 150° C. for 20 minutes.

The dry bulk, wet bulk and fluff absorbance quality (FAQ) of the product was next determined. A measured quantity of pulp was air laid into a mat in a plexiglas cylinder tube. A pressure of 0.6 kPa was exerted on the mat and the volume (dry bulk) of the mat was measured to give a measure of its dry compressibility. Next, a pressure of 2.5 kPa was placed on the mat, and the mat volume (dry bulk) was again measured. Water was then introduced into the bottom of the cylinder to determine the amount of water absorbed by the fluff under a pressure of 2.5 kPa, and this amount of water (wet bulk) was measured. The FAQ capacity is expressed as the grams of water absorbed per gram of pulp, and this value is an indication of the absorbency of the crosslinked fibers. Table I illustrates that the N-sulfatosuccinimide crosslinking agent of this example significantly enhanced the FAQ capacity and bulk of a handsheet.

TABLE I

FAQ CAPACITY AND BULK OF UNTREATED AND TREATED MAT

|  | FAQ Capacity | Hand Sheet Bulk (2:1 Treated pulp: Buckeye pulp) |
|---|---|---|
| Untreated pulp | 11.6 g/g | 5.4 cc/g |
| Pulp treated with 10% Compound I | 16.5 g/g | 12.0 cc/g |

The N-sulfatosuccinimide crosslinking agent was similarly tested at a variety of reactant and catalyst concentrations. The results of those runs are shown in the following Tables IIA and IIB, wherein all concentrations are on a wt/wt % of solids basis. Handsheets are made from a 2:1 mixture of treated crosslinked NF105 pulp:Buckeye Pulp (Buckeye Pulp may be obtained from Procter and Gamble of Cincinnati, Ohio).

TABLE IIA

PROPERTIES OF N-SULFATOSUCCINIMIDE TREATED MATS

| Run | Reactants | Catalyst | Reactant Conc. | Catalyst Conc. | Cure Temp | Cure Time | Color | Dry Bulk 0.6 kPa |
|---|---|---|---|---|---|---|---|---|
| 1 | Pyridinium N-Sulfatosuccinimide | NaHCO$_3$ | 10% | 6.7% | 150° C. | 20 min | lt. cream | 47.4 |
| 2 | Pyridinium N-Sulfatosuccinimide | NaNCO$_3$ | 10% | 3.1% | 150° C. | 20 min | white |  |
| 3 | Pyridinium N-Sulfatosuccinimide | NaHCO$_3$ | 10% | 6.1% | 150° C. | 20 min | lt. cream |  |
| 4 | Pyridinium N-Sulfatosuccinimide | NaHCO$_3$ | 10% | (12.1%) | 150° C. | 20 min | cream |  |
| 5 | Pyridinium N-Sulfatosuccinimide | NaNCO$_3$ | 10% | (24.3%) | 150° C. | 20 min | cream |  |
| 6 | Pyridinium N-Sulfatosuccinimide | NaNCO$_3$ | 5% | 3.0% | 150° C. | 20 min | lt. cream |  |
| 7 | Pyridinium N-Sulfatosuccinimide | NaHCO$_3$ | 20% | 12.1% | 150° C. | 20 min | lt. cream |  |
| 8 | Pyridinium N-Sulfatosuccinimide | none | 10% | none | 150° C. | 20 min | lt. tan | 46.5 |
| 9 | Pyridinium N-Sulfatosuccinimide | Na$_2$CO$_3$ | 10% | 6.7% | 150° C. | 20 min | cream | 51.1 |

TABLE IIA-continued

PROPERTIES OF N-SULFATOSUCCINIMIDE TREATED MATS

| Run | Reactants | Catalyst | Reactant Conc. | Catalyst Conc. | Cure Temp | Cure Time | Color | Dry Bulk 0.6 kPa |
|---|---|---|---|---|---|---|---|---|
| 10 | Pyridinium N-Sulfatosuccinimide | NaHCO$_3$ | 10.0% | 6.1% | max. | | pp | 51.9 |
| 11 | Pyridinium N-Sulfatosuccinimide | NaHCO$_3$ | 10.0% | 6.1% | 150° C. | 15 min | | 52.8 |

TABLE IIB

PROPERTIES OF N-SULFATOSUCCINIMIDE TREATED MATS

| Run | Reactants | Dry Bulk 2.5 kPa | Absorb Time | Wet Bulk 2.5 kPa | Wet Bulk 0.6 kPa | FAQ Capacity | Bulk (cc/g) | Permeabitity (cu ft/sq ft) |
|---|---|---|---|---|---|---|---|---|
| 1 | Pyridinium N-Sulfatosuccinimide | 26.5 | 6.3 | 12.8 | 15.7 | 16.5 | 12.0 | 95 |
| 2 | Pyridinium N-Sulfatosuccinimide | | | | | | 4.6 | 23 |
| 3 | Pyridinium N-Sulfatosuccinimide | | | | | | 10.1 | 78 |
| 4 | Pyridinium N-Sulfatosuccinimide | | | | | | 8.9 | 68 |
| 5 | Pyridinium N-Sulfatosuccinimide | | | | | | 7.7 | 53 |
| 6 | Pyridinium N-Sulfatosuccinimide | | | | | | 9.8 | 68 |
| 7 | Pyridinium N-Sulfatosuccinimide | | | | | | 11.2 | 91 |
| 8 | Pyridinium N-Sulfatosuccinimide | | | | | | 5.9 | 33 |
| 9 | Pyridinium N-Sulfatosuccinimide | 28.4 | 6.2 | 9.4 | 11.2 | 12.1 | | |
| 10 | Pyridinium N-Sulfatosuccinimide | 27.4 | 4.9 | 12.4 | 15.0 | 15.5 | 8.5 | 73 |
| 11 | Pyridinium N-Sulfatosuccinimide | 28.1 | 5.0 | 13.4 | 16.1 | 16.5 | 10.3 | 87 |

All concentrations are on a wt/wt % solids basis, except those in parentheses, which are on a wt/wt % solution "as is" basis. Better bulk results were noted when the ratio of crosslinking agent to catalyst was about 2:1 or more of catalyst. Crosslinking concentrations of 5–20%, preferably 5–10%, most preferably 10%, were used.

EXAMPLE II

Crosslinking with 2,2'dimethoxyethanal

In this example, 2,2'-dimethoxyethanal (DME) was used as the crosslinking agent. DME was obtained from Hoechst Celanese Corporation, Specialty Chemicals Division in Charlotte, N.C. DME has the structural formula shown below:

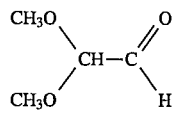

Name: 2,2 dimethoxyacetaldehyde
  Glyoxal dimethylacetal
  Dimethoxyacetaldehyde
Formula: C$_4$H$_8$O$_3$ DME is a colorless liquid with a fruity odor, a molecular weight of 101.4, a boiling point of 65° C. at 140 mm Hg, and a pH at 20° C. of 7. The DME was completely miscible in water at 20° C. and had a viscosity of 0.28 and a density of 1.173 at 20° C.

The DME and catalyst were dissolved in 10 ml of water. The water phase was then diluted to 15.5 ml with water and immediately distributed dropwise over the surface of a 16.5 g piece of pulpsheet from NF105 pulp. The NF105 pulpsheet was treated with the aqueous solution of DME, catalyst and urea derivative (if any) to a 50% consistency level, then fiberized and cured at 150° C. for 20 minutes. The results are shown in the following Table III, where all concentrations are on a wt/wt % solids basis, except those in parentheses which are in a wt/wt % solution "as is" (molar) basis. Handsheets are from a 2:1 mixture of crosslinked NF105 pulp:Buckeye pulp. Numerical color ratings in Table II are: 0=no color, bright; 1=trace of color, but possibly acceptable; 2=very noticeable color, probably not acceptable; 3=intense color.

TABLE IIIA

PROPERTIES OF DME TREATED MATS

| Run | Reactants | Catalyst | Reactant Conc. | Catalyst Conc. | Cure Temp | Cure Time | Color | Dry Bulk 0.6 kPa |
|---|---|---|---|---|---|---|---|---|
| 1 | DME | $Al_2(SO_4)_3$ | 9.0% | 2.0% | 150° C. | 20 mi | 1 | 49.7 |
| 2 | DME + Urea (2:1) | $Zn(NO_3)_2$ | 9% DME | 2.0% | 150° C. | 20 mi | 2 | 52.1 |
| 3 | DME + 2-Imida-zolidone (2:1) | $Zn(NO_3)_2$ | 9% DME | 2.0% | 150° C. | 20 mi | 1 | 50.8 |
| 4 | DME + 2-Imida-zolidone (2:1) | $Zn(NO_3)_2$ | 13.5% | 3.0% | 150° C. | 20 mi | 1 | 51.1 |
| 5 | DME + 2-Imida-zolidone (2:1) | $Zn(NO_3)_2$ | 9% DME | 2.0% | 150° C. | 20 mi | 1 | 51.3 |
| 6 | DME + 2-Imida-zolidone (2:1) | $Zn(NO_3)_2$ | 4.5% DME | 1.0% | 150° C. | 20 mi | 1 | 50.5 |
| 7 | DME + 2-Imida-zolidone (2:1) | $Zn(NO_3)_2$ | 2.3% DME | .5% | 150° C. | 20 mi | 1 | 48.9 |

TABLE IIIB

PROPERTIES OF DME TREATED MATS

| Run | Reactants | Dry Bulk 2.5 kPa | Absorb Time | Wet Bulk 2.5 kPa | Wet Bulk 0.6 kPa | FAQ Capacity | Bulk (cc/g) | Permeability (cu ft/sq ft) |
|---|---|---|---|---|---|---|---|---|
| 1 | DME | 29.2 | 7.7 | 15.6 | 18.5 | 18.8 | 12.9 | 103 |
| 2 | DME + Urea (2:1) | 30.2 | 7.9 | 15.3 | 18.0 | 18.2 | 12.1 | 88 |
| 3 | DME + 2-Imida-zolidone (2:1) | 28.5 | 4.9 | 15.1 | 18.6 | 18.8 | 16.2 | 108 |
| 4 | DME + 2-Imida-zolidone (2:1) | 29.3 | 4.8 | 15.0 | 18.2 | 18.8 | 11.9 | 99 |
| 5 | DME + 2-Imida-zolidone (2:1) | 29.1 | 5.6 | 14.9 | 18.1 | 18.6 | 11.5 | 103 |
| 6 | DME + 2-Imida-zolidone (2:1) | 28.6 | 6.5 | 13.9 | 16.7 | 17.2 | 10.0 | 75 |
| 7 | DME + 2-Imida-zolidone (2:1) | 27.6 | 5.7 | 12.2 | 14.5 | 15.2 | 7.2 | 88 |

EXAMPLE III

Periodate Crosslinking

An NB316 pulp from the Weyerhaeuser Company was treated with the sodium periodate in an aqueous slurry for 2–4 days at 22° C. The slurry was filtered and the pulp mat was washed several times with water and air dried. The catalyst was then added and the crosslinking reaction carried out at high temperatures, as in Example II above. This fiber had high absorbency and was easily densified by pressure application into an air-laid pad form to 0.2–0.3 g/cc and the pad exhibited higher total capacity and better wicking properties than uncrosslinked NB316 at a similar density. Total capacity and wicking were measured as in Example VI below. It was also found that when the sodium periodate oxycellulose was treated with 2% (wt/wt) alum and treated to 100°–150° C. for 20 minutes, the resulting fiber exhibited high bulk properties in a wet-laid handsheet when combined with Buckeye pulp in a 2:1 ratio. Densification of the crosslinked cellulose is more fully described in copending U.S. patent application Ser. No. 07/665,761 filed Mar. 7, 1991, which is incorporated by reference. The results with undensified material are reported in Table IV below, while results with a densified pad are shown in Table V below.

TABLE IV

PROPERTIES OF PERIODATE CROSSLINKED NON-DENSIFIED CELLULOSE

| Reactants | FAQ Capacity | FAQ Absorption Time | Handsheet Bulk |
|---|---|---|---|
| NB316 Periodate Oxycelluose | 16.8 g/g | 5.7 sec | 6.0 cc/g |
| NB316 Periodate Oxycellulose + alum | 19.8 g/g | 5.8 sec | 10.8 cc/g |
| NF105 | 11.6 g/g | 5.0 sec | 4.7 cc/g |

TABLE V

PROPERTIES OF PERIODATE CROSSLINKED DENSIFIED CELLULOSE

| Reactants | Total Capacity | Wicking Capacity | Wicking Time |
|---|---|---|---|
| NB316 Periodate Oxycellulose | 16.1 g/g | 9.9 g/g | 19 sec |
| NB316 | 9.6 g/g | 7.5 g/g | 40 sec |

Crosslinking in non-densified pads was studied using a variety of catalysts and reaction conditions shown in Table VI below, where all concentrations are on a wt/wt % solids basis (expressing the concentration of reactants as a weight percentage of the final treated product). Handsheets are again from a 2:1 mixture of additive pulp:Buckeye pulp. Numerical color ratings are the same as the Example II above. The pulp used in these runs was NB316.

TABLE VIA

PERIODATE CROSSLINKING WITH VARIOUS CATALYSTS AND CONDITIONS

| Run | Reactant | Catalyst | Reactant Conc. | Catalyst Conc. | Cure Temp | Cure Time | Color | Dry Bulk 0.6 kPa |
|---|---|---|---|---|---|---|---|---|
| 1 | Sodium Periodate | none | 6.4% | 0.0% | 150° C. | 20 min | 0 | 30.4 |
| 2 | Sodium Periodate | $Al_2(SO_4)_3$ | 6.4% | 2.0% | 150° C. | 20 min | 2 | 38.2 |
| 3 | Sodium Periodate | $Zn(NO_3)_2$ | 6.4% | 2.0% | 150° C. | 20 min | 1 | 43.5 |
| 4 | Sodium Periodate | DEG + $Zn(NO_3)_2$ | 6.4% | 3% + 2% | 150° C. | 20 min | 1 | 43.0 |
| 5 | Sodium Periodate | ethylenediamine | 6.4% | 2.0% | 150° C. | 20 min | 2 | |
| 6 | Sodium Periodate | ethylenediamine $Al(SO_4)_3$ | 6.4% | 2% + 1% | 150° C. | 20 min | 3 | |
| 7 | Sodium Periodate | none | 3.3% | 0.0% | 155° C. | 20 min | 1 | 43.2 |
| 8 | Sodium Periodate | $Al_2(SO_4)_3$ | 3.3% | 2.0% | 155° C. | 20 min | 2 | 38.9 |
| 9 | Sodium Periodate | $Zn(NO_3)_2$ | 3.3% | 1.0% | 155° C. | 20 min | 1 | |
| 10 | Sodium Periodate | DEG + $Zn(NO_3)_2$ | 3.3% | 3% + 2% | 155° C. | 20 min | 2 | 41.2 |
| 11 | Sodium Periodate | Urea + $Zn(NO_3)_2$ | 3.3% | 10% + 2% | 155° C. | 20 min | 2 | |
| 12 | Sodium Periodate | Urea | 3.3% | 10.0% | 150° C. | 20 min | 2 | |
| 13 | Sodium Periodate | none | 12.8% | 0.0% | 155° C. | 20 min | 0 | 42.3 |
| 14 | Sodium Periodate | $Al_2(SO_4)_3$ | 12.8% | 2.0% | 155° C. | 20 min | 3 | 39.6 |
| 15 | Sodium Periodate | $Al_2(SO_4)_3$ | 12.8% | 2.0% | 150° C. | 20 min | 2 | 43.7 |
| 16 | Sodium Periodate | $Al_2(SO_4)_3$ | 12.8% | 2.0% | 125° C. | 20 min | 1 | 47.1 |
| 17 | Sodium Periodate | $Al_2(SO_4)_3$ | 12.8% | 2.0% | 100° C. | 20 min | 0 | 47.4 |
| 18 | Sodium Periodate | $Zn(NO_3)_2$ | 12.8% | 1.0% | 155° C. | 20 min | 2 | 42.9 |
| 19 | Sodium Periodate | DEG + $Zn(NO_3)_2$ | 12.8% | 3% + 2% | 155° C. | 20 min | 3 | 39.3 |
| 20 | Sodium Periodate | Urea + $Zn(NO_3)_2$ | 12.8% | 10% + 2% | 155° C. | 20 min | 3 | |
| 21 | Sodium Periodate | Urea | 12.8% | 10.0% | 155° C. | 20 min | 2 | |
| 22 | Sodium Periodate | $NaHSO_3$ | 12.8% | 5.0% | 150° C. | 20 min | 1 | 40.0 |
| 23 | Sodium Periodate | $NH_4Cl$ | 12.8% | 5.0% | 150° C. | 20 min | 3 | |
| 24 | Sodium Periodate | HCl | 12.8% | 1.0% | 150° C. | 20 min | 3 | 33.6 |
| 25 | Sodium Periodate | $MgCl_2$ | 12.8% | 2.0% | 150° C. | 20 min | 2 | 44.3 |
| 26 | Sodium Periodate | $(NH_4)SO_4$ | 12.8% | 2.0% | 150° C. | 20 min | 2 | |
| 27 | Sodium Periodate | $NH_4OH$ | 12.8% | 10.0% | 150° C. | 20 min | 3 | |
| 28 | Sodium Periodate | Borax | 12.8% | 2.0% | 150° C. | 20 min | 1 | |
| 29 | Sodium Periodate | $(NH_4)_2HPO$ (dibasic) | 12.8% | 2.0% | 150° | 20 min | 3 | |
| 30 | Sodium Periodate | $NH_4H_2PO_4$ (monobasic) | 12.8% | 2.0% | 150° | 20 min | 3 | |
| 31 | Sodium Periodate | none | 12.8% | 0.0% | none | none | 0 | 48.8 |

40

TABLE VIB

PERIODATE CROSSLINKING WITH VARIOUS CATALYSTS AND CONDITIONS

| Run | Reactants | Dry Bulk 2.5 kPa | Absorb Time | Wet Bulk 2.5 kPa | Wet Bulk 0.6 kPa | FAQ Capacity | Bulk (cc/g) | Permeability (cu ft/sq ft) |
|---|---|---|---|---|---|---|---|---|
| 1 | 6.4% Sodium Periodate | 12.8 | 4.8 | 12.9 | 15.2 | 15.3 | 5.6 | 27 |
| 2 | 6.4% Sodium Periodate | 25.4 | 5.0 | 13.4 | 16.1 | 16.8 | 9.6 | 72 |
| 3 | 6.4% Sodium Periodate | 27.5 | 5.0 | 13.5 | 16.0 | 16.7 | 7.9 | 49 |
| 4 | 6.4% Sodium Periodate | 26.4 | 3.8 | 12.6 | 14.9 | 15.8 | 7.4 | 47 |
| 5 | 6.4% Sodium Periodate | | | | | | 5.2 | 32 |
| 6 | 6.4% Sodium Periodate | | | | | | 8.2 | 76 |
| 7 | 3.3% Sodium Periodate | 26.7 | 6.8 | 12.1 | 14.1 | 14.8 | 4.3 | 51 |
| 8 | 3.3% Sodium Periodate | 25.1 | 7.8 | 13.2 | 15.5 | 16.2 | 7.6 | 65 |
| 9 | 3.3% Sodium Periodate | | | | | | 6.4 | 44 |
| 10 | 3.3% Sodium Periodate | 25.3 | 5.3 | 12.4 | 14.4 | 15.0 | 6.7 | 36 |
| 11 | 3.3% Sodium Periodate | | | | | | 6.0 | 44 |
| 12 | 6.3% Sodium Periodate | | | | | | 5.6 | 44 |
| 13 | 12.8% Sodium Periodate | 26.6 | 10.4 | 13.0 | 15.5 | 16.2 | 5.4 | 27 |
| 14 | 12.8% Sodium Periodate | 26.3 | 18.3 | 15.6 | 18.4 | 19.1 | 10.3 | 81 |
| 15 | 12.8% Sodium Periodate | 27.7 | 5.8 | 15.9 | 18.8 | 19.8 | 10.8 | 87 |
| 16 | 12.8% Sodium Periodate | 28.9 | 4.3 | 14.8 | 17.6 | 18.8 | 10.0 | 73 |
| 17 | 12.8% Sodium Periodate | 28.7 | 4.4 | 13.6 | 16.3 | 17.4 | 8.6 | 53 |
| 18 | 12.8% Sodium Periodate | 27.5 | 14.7 | 14.3 | 17.1 | 18.1 | 8.8 | 51 |
| 19 | 12.8% Sodium Periodate | 25.5 | 11.1 | 13.9 | 16.4 | 17.1 | 8.3 | 55 |

TABLE VIB-continued

PERIODATE CROSSLINKING WITH VARIOUS CATALYSTS AND CONDITIONS

| Run | Reactants | Dry Bulk 2.5 kPa | Absorb Time | Wet Bulk 2.5 kPa | Wet Bulk 0.6 kPa | FAQ Capacity | Bulk (cc/g) | Permeability (cu ft/sq ft) |
|---|---|---|---|---|---|---|---|---|
| 20 | 12.8% Sodium Periodate | | | | | | 7.4 | 44 |
| 21 | 12.8% Sodium Periodate | | | | | | 6.4 | 44 |
| 22 | 12.8% Sodium Periodate | 24.5 | 3.6 | 9.5 | 11.8 | 12.8 | 5.8 | 39 |
| 23 | 12.8% Sodium Periodate | | | | | | 9.6 | 77 |
| 24 | 12.8% Sodium Periodate | 23.8 | 5.3 | 16.9 | 19.6 | 20.3 | 11.3 | 104 |
| 25 | 12.8% Sodium Periodate | 28.1 | 7.3 | 14.5 | 17.3 | 18.2 | 9.6 | 84 |
| 26 | 12.8% Sodium Periodate | | | | | | 8.1 | 60 |
| 27 | 12.8% Sodium Periodate | | | | | | 6.6 | 43 |
| 28 | 12.8% Sodium Periodate | | | | | | 6.2 | 36 |
| 29 | 12.8% Sodium Periodate | | | | | | 8.9 | 69 |
| 30 | 12.8% Sodium Periodate | | | | | | 8.7 | 69 |
| 31 | 12.8% Sodium Periodate | 29.0 | 5.7 | 13.0 | 15.8 | 16.8 | 6.0 | 39 |

EXAMPLE IV

Sulfonyldiethanol Crosslinking

An NF105 pulp was crosslinked as in Example III, except the following reactants and catalysts were substituted for the previous reactants and catalysts. The results are shown in Tables VIIA and VIIB.

TABLE VIIA

SULFONYLDIETHANOL CROSSLINKING WITH VARIOUS CATALYSTS AND CONDITIONS

| Run | Reactants | Catalyst | Reactant Conc. | Catalyst Conc. | Cure Temp | Cure Time | Color | Dry Bulk 0.6 kPa |
|---|---|---|---|---|---|---|---|---|
| 1 | Sulfonyldiethanol | none | 10% | none | 150° C. | 20 min | | |
| 2 | Sulfonyldiethanol | NaOH | 10% | 1.3% | 150° C. | 20 min | | 51.1 |
| 3 | Sulfonyldiethanol | NaOH | 10% | 2.7% | 150° C. | 20 min | | 50.3 |
| 4 | Sulfonyldiethanol | NaOH | 10% | 5.3% | 150° C. | 20 min | | 48.8 |
| 5 | Sulfonyldiethanol | NaHCO$_3$ | 10% | 5.6% | 150° C. | 20 min | | 54.0 |
| 6 | Sulfonyldiethanol | NaOH | 10% | 0.7% | 150° C. | 20 min | 1 | 45.7 |
| 7 | Sulfonyldiethanol | NaOH | 10% | 2.0% | 150° C. | 20 min | 2 | 51.6 |
| 8 | Sulfonyldiethanol | NaHCO$_3$ | 10% | 2.8% | 150° C. | 20 min | 2 | 50.2 |
| 9 | Sulfonyldiethanol | Al$_2$(SO$_4$)$_3$ | 10% | 2.0% | 150° C. | 20 min | 0 | |
| 10 | Sulfonyldiethanol | Zn(NO$_3$)$_2$ | 10% | 2.0% | 150° C. | 20 min | 1 | |
| 11 | Sulfonyldiethanol | NaH$_2$PO$_2$ | 10% | 2.0% | 150° C. | 20 min | 1 | |
| 12 | Sulfonyldiethanol | NaOH | 7.5% | 1.5% | 150° C. | 20 min | 2 | 49.4 |
| 13 | Sulfonyldiethanol | NaOH | 5% | 1.0% | 150° C. | 20 min | 2 | 49.0 |
| 14 | Sulfonyldiethanol | NaOH | 2.5% | 0.5% | 150° C. | 20 min | 1 | 49.7 |
| 15 | Sulfonyldiethanol | Na$_2$HPO$_4$ | 10% | 9.2% | 150° C. | 20 min | 0 | |
| 16 | Sulfonyldiethanol | Na$_3$PO$_4$ + 12H$_2$O | 10% | 24.6% | 150° C. | 20 min | 2 | 46.6 |
| 17 | Sulfonyldiethanol | Na$_2$HPO$_4$ + Na$_3$PO$_4$·12H$_2$O | 10% | 4.6% + 12.2% | 150° C. | 20 min | 1 | 43.1 |
| 18 | Sulfonyldiethanol | Sodium borate + 10H$_2$O | 10% | 25.0% | 150° C. | 20 min | 0 | |
| 19 | 2,2'-Sulfonyldiethanol | NaOH | 10.0% | 1.3% | max. | pp | 2 | 51.3 |
| 20 | 2,2'-Sulfonyldiethanol | NaOH | 10.0% | 1.3% | 150° C. | 15 min | 2 | |

TABLE VIIB

SULFONYLDIETHANOL CROSSLINKING WITH VARIOUS CATALYSTS AND CONDITIONS

| Run | Reactants | Dry Bulk 2.5 kPa | Absorb Time | Wet Bulk 2.5 kPa | Wet Bulk 0.6 kPa | FAQ Capacity | Bulk (cc/g) | Permeability (cu ft/sq ft) |
|---|---|---|---|---|---|---|---|---|
| 1 | Sulfonyldiethanol | | | | | | 3.8 | 19 |
| 2 | Sulfonyldiethanol | 28.5 | 7.5 | 15.5 | 18.7 | 19.0 | 14.8 | 108 |
| 3 | Sulfonyldiethanol | 28.7 | 7.3 | 15.2 | 18.8 | 19.0 | 13.9 | 121 |
| 4 | Sulfonyldiethanol | 27.6 | 7.2 | 13.4 | 17.2 | 17.8 | 13.3 | 104 |
| 5 | Sulfonyldiethanol | 30.3 | 8.7 | 15.4 | 19.2 | 19.3 | 13.5 | 118 |
| 6 | Sulfonyldiethanol | 25.6 | 5.0 | 11.7 | 14.2 | 14.7 | 7.4 | 59 |
| 7 | Sulfonyldiethanol | 28.8 | 7.3 | 15.3 | 18.9 | 19.0 | 16.0 | 124 |
| 8 | Sulfonyldiethanol | 27.9 | 6.9 | 14.8 | 18.3 | 18.4 | 13.5 | 108 |
| 9 | Sulfonyldiethanol | | | | | | 4.8 | 27 |
| 10 | Sulfonyldiethanol | | | | | | 3.9 | 22 |
| 11 | Sulfonyldiethanol | | | | | | 3.7 | 15 |
| 12 | Sulfonyldiethanol | 27.4 | 6.9 | 14.0 | 17.3 | 18.1 | 14.6 | 111 |
| 13 | Sulfonyldiethanol | 27.3 | 6.9 | 13.3 | 16.5 | 17.9 | 13.2 | 109 |
| 14 | Sulfonyldiethanol | 27.2 | 6.0 | 11.4 | 14.0 | 15.4 | 8.9 | 63 |
| 15 | Sulfonyldiethanol | | | | | | 5.3 | 23 |
| 16 | Sulfonyldiethanol | 24.5 | 5.9 | 11.3 | 15.0 | 16.6 | 12.6 | 105 |
| 17 | Sulfonyldiethanol | 23.1 | 4.6 | 9.9 | 12.7 | 14.4 | 9.4 | 76 |
| 18 | Sulfonyldiethanol | | | | | | 4.5 | 25 |
| 19 | 2,2'-Sulfonyl-diethanol[1] | 27.4 | 6.0 | 12.2 | 14.6 | 14.9 | 7.4 | 60 |
| 20 | 2,2'-Sulfonyl-diethanol[2] | | | | | | 10.6 | 88 |

[1]This test was performed at a pilot plant in a semi-commercial process instead of a small-scale laboratory experiment, as in the other runs.
[2]Post-cured in an oven.

EXAMPLE V

Glyoxal and Imidazolidone Crosslinking

An NF105 pulp was crosslinked as in Example III, except the reactants and catalysts shown in Tables VIIIA and VIIIB were substituted for the previous reactants and catalysts. Handsheets are again from a 2:1 mixture of additive pulp::Buckeye pulp. All concentrations are again on a wt/wt % solids basis, except those in parentheses which are in a wt/wt % solution "as is" (molar) basis.

TABLE VIIIA

GLYOXAL + IMIDAZOLIDONE CROSSLINKING WITH VARIOUS CATALYSTS AND CONDITIONS

| Run | Reactants | Catalyst | Reactant Conc. | Catalyst Conc. | Cure Temp | Cure Time | Color | Dry Bulk 0.6 kPa |
|---|---|---|---|---|---|---|---|---|
| 1 | Glyoxal + 2-Imidazolidone (2:1) | $Zn(NO_3)_2$ | 5% + 3.7% | 2.0% | 150° C. | 20 min | 1 | 52.5 |
| 2 | Glyoxal + 2-Imidazolidone (2:1) | $Zn(NO_3)_2$ | 5% + 3.7% | 2.0% | 150° C. | 20 min | 1 | 52.6 |
| 3 | Glyoxal + 2-Imidazolidone (2:1) | none | 5% + 3.7% | 0.0% | 150° C. | 20 min | 1 | |
| 4 | Glyoxal + 2-Imidazolidone (2:1) | $Al_2(SO_4)_3$ | 5% + 3.7% | 2.0% | 150° C. | 20 min | 2 | |
| 5 | Glyoxal + 2-Imidazolidone (2:1) | $NaHCO_3$ | 5% + 3.7% | 1.0% | 150° C. | 20 min | 2 | |
| 6 | Glyoxal + 2-Imidazolidone (2:1) | $Zn(NO_3)_2$ | 3.8% + 2.8 | 1.5% | 150° C. | 20 min | 1 | 51.5 |
| 7 | Glyoxal + 2-Imidazolidone (2:1) | $Zn(NO_3)_2$ | 2.5% + 1.9 | 1.0% | 150° C. | 20 min | 1 | 53.0 |
| 8 | Glyoxal + 2-Imidazolidone (2:1) | $Zn(NO_3)_2$ | 1.3% + 0.9 | .5% | 150° C. | 20 min | 1 | 50.5 |
| 9 | Glyoxal/2-Imidazolidone Rxn Prod. | none | 8.7% | 0.0% | 150° C. | 20 min | 2 | |
| 10 | Glyoxal/2-Imidazolidone Rxn Prod. | $Zn(NO_3)_2$ | 8.7% | 2.0% | 150° C. | 20 min | 1 | 51.5 |
| 11 | Glyoxal/2-Imidazolidone Rxn Prod. | $Al_2(SO_4)_3$ | 8.7% | 2.0% | 150° C. | 20 min | 1 | 49.6 |
| 12 | Glyoxal + 2-Imidazolidone (1:1) | $Zn(NO_3)_2$ | 5% + 7.4% | 2.0% | 150° C. | 20 min | 1 | 53.5 |
| 13 | Glyoxal + 2-Imidazolidone (3:1) | $Zn(NO_3)_2$ | 5% + 2.5% | 2.0% | 150° C. | 20 min | 1 | 53.2 |
| 14 | Glyoxal + 2-Imidazolidone(2:1) | $Zn(NO_3)_2$ | 5% + 3.7% | 2.0% | max. | pp | 1 | 58.3 |
| 15 | Glyoxal + 2-Imidazolidone(2:1) | $Zn(NO_3)_2$ | 5% + 3.7% | 2.0% | 150° C. | 15 min | 1 | 56.1 |
| 16 | Glyoxal + 2-Imidazolidone(2:1) | none | 5% + 3.7% | 0.0% | max. | pp | 0 | 58.2 |
| 17 | Glyoxal + 2-Imidazolidone(2:1) | $Zn(NO_3)_2$ | 5% + 3.7% | 4.0% | max. | pp | 1 | 54.0 |
| 18 | Glyoxal + 2-Imidazolidone(2:1) | $Zn(NO_3)_2$ | 5% + 3.7% | 4.0% | 150° C. | 15 mi | 2 | 51.7 |
| 19 | Glyoxal + 2-Imidazolidone(2:1) | $AlCl_3/MgCl$ (Aerotex 9) | 5% + 3.7% | .23% + 2.6 (9.3%) | max. | pp | 1 | 48.4 |
| 20 | Glyoxal + 2-Imidazolidone(2:1) | $Al_2(SO_4)_3$ | 5% + 3.7% | 2.0% | max. | pp | 0 | 54.7 |
| 21 | Glyoxal + 2-Imidazolidone(2:1) | $Al_2(SO_4)_3$ | 5% + 3.7% | 2.0% | 150° C. | 15 mi | 2 | 52.3 |
| 22 | Glyoxal + 2-Imidazolidone(2:1) | $Zn(NO_3)_2$ | 10% + 7.4% | 4.0% | max. | pp | 2 | 53.0 |
| 23 | Glyoxal + 2-Imidazolidone(2:1) | $Zn(NO_3)_2$ | 3.8% + 2.8 | 1.5% | max. | pp | 1 | 56.0 |
| 24 | Glyoxal + 2-Imidazolidone(2:1) | $Zn(NO_3)_2$ | 3.8% + 2.8 | 1.5% | 150° C. | 15 mi | 1 | 40.2 |
| 25 | Glyoxal + 2-Imidazolidone(2:1) | $Zn(NO_3)_2$ | 2.5% + 1.9 | 1.0% | max. | pp | 0 | 55.7 |
| 26 | Glyoxal + 2-Imidazolidone(2:1) | $Zn(NO_3)_2$ | 5% + 3.7% | 1.0% | max. | pp | 0 | 57.9 |

TABLE VIIIB

GLYOXAL + IMIDAZOLIDONE CROSSLINKING WITH VARIOUS CATALYSTS AND CONDITIONS

| Run | Reactants | Dry Bulk 2.5 kPa | Absorb Time | Wet Bulk 2.5 kPa | Wet Bulk 0.6 kPa | FAQ Capacity | Bulk (cc/g) | Permeability (cu ft/sq ft) |
|---|---|---|---|---|---|---|---|---|
| 1 | Glyoxal + 2-Imidazolidone (2:1) | 30.7 | 15.3 | 17.9 | 21.6 | 20.3 | 14.7 | 124 |
| 2 | Glyoxal + 2-Imidazolidone (2:1) | 30.4 | 17.5 | 18.3 | 21.8 | 20.3 | 12.2 | 104 |
| 3 | Glyoxal + 2-Imidazolidone (2:1) | | | | | | 8.1 | 50 |
| 4 | Glyoxal + 2-Imidazolidone (2:1) | | | | | | 12.3 | 102 |
| 5 | Glyoxal + 2-Imidazotidone (2:1) | | | | | | 5.2 | 27 |

TABLE VIIIB-continued

GLYOXAL + IMIDAZOLIDONE CROSSLINKING WITH VARIOUS CATALYSTS AND CONDITIONS

| Run | Reactants | Dry Bulk 2.5 kPa | Absorb Time | Wet Bulk 2.5 kPa | Wet Bulk 0.6 kPa | FAQ Capacity | Bulk (cc/g) | Permeability (cu ft/sq ft) |
|---|---|---|---|---|---|---|---|---|
| 6 | Glyoxal + 2-Imidazolidone (2:1) | 29.8 | 10.4 | 17.7 | 21.1 | 20.3 | 13.4 | 83 |
| 7 | Glyoxal + 2-Imidazolidone (2:1) | 30.4 | 9.6 | 16.3 | 19.4 | 19.4 | 11.5 | 73 |
| 8 | Glyoxal + 2-Imidazolidone (2:1) | 28.2 | 6.6 | 13.5 | 16.2 | 16.7 | 8.5 | 55 |
| 9 | Glyoxal/2-Imidazolidone Rxn Prod. | | | | | | 6.8 | 42 |
| 10 | Glyoxal/2-Imidazolidone Rxn Prod. | 29.7 | 9.6 | 17.0 | 20.3 | 19.7 | 12.0 | 91 |
| 11 | Glyoxal/2-Imidazolidone Rxn Prod. | 29.7 | 14.7 | 18.0 | 21.7 | 19.6 | 11.4 | 90 |
| 12 | Glyoxal + 2-Imidazolidone (1:1) | 31.4 | 16.5 | 18.5 | 22.2 | 20.2 | 13.2 | 114 |
| 13 | Glyoxal + 2-Imidazolidone (3:1) | 30.6 | 9.0 | 16.2 | 19.2 | 18.6 | 8.8 | 60 |
| 14 | Glyoxal + 2-Imidazolidone(2:1) | 32.8 | 23.2 | 16.9 | 20.4 | 18.0 | 8.5 | 69 |
| 15 | Glyoxal + 2-Imidazolidone(2:1) | 31.9 | 21.8 | 16.9 | 20.4 | 18.3 | 11.1 | 77 |
| 16 | Glyoxal + 2-Imidazolidone(2:1) | 32.5 | 13.1 | 14.7 | 17.8 | 17.1 | 6.5 | 47 |
| 17 | Glyoxal + 2-Imidazolidone(2:1) | 31.1 | 20.6 | 16.3 | 19.8 | 17.7 | 9.1 | 79 |
| 18 | Glyoxal + 2-Imidazolidone(2:1) | 30.2 | 16.4 | 15.8 | 19.2 | 17.8 | 9.7 | 76 |
| 19 | Glyoxal + 2-Imidazolidone(2:1) | 28.8 | 11.7 | 15.4 | 19.0 | 17.3 | 8.8 | 81 |
| 20 | Glyoxal + 2-Imidazolidone(2:1) | 31.9 | 26.3 | 17.7 | 21.6 | 18.9 | 9.3 | 82 |
| 21 | Glyoxal + 2-Imidazolidone(2:1) | 31.3 | 59.8 | 19.6 | 24.0 | 18.8 | 11.2 | 96 |
| 22 | Glyoxal + 2-Imidazolidone(2:1) | 31.4 | 62.5 | 18.1 | 22.3 | 17.5 | 9.6 | 95 |
| 23 | Glyoxal + 2-Imidazolidone(2:1) | 31.1 | 17.3 | 16.7 | 20.3 | 18.4 | 9.8 | 80 |
| 24 | Glyoxal + 2-Imidazolidone(2:1) | 16.3 | 19.6 | 12.1 | 15.7 | 18.8 | 10.3 | 78 |
| 25 | Glyoxal + 2-Imidazolidone(2:1) | 30.5 | 10.5 | 15.1 | 18.3 | 17.6 | 7.7 | 59 |
| 26 | Glyoxal + 2-Imidazolidone(2:1) | 31.6 | 17.6 | 16.8 | 20.5 | 18.3 | 8.3 | 68 |

EXAMPLE VI

Pad Compression and Wetting Test

The following procedure was utilized to determine the wicking properties and capacity of absorbent materials crosslinked with the crosslinking agents shown in Table IX.

The wicking properties were determined by cutting an absorbent test material into a 10 cm by 10 cm sample. The test sample was placed in a room at 50% humidity to equilibrate for 24 hours. A glass plate 30.5 cm by 15 cm wamarked with four 1 inch marks at a bottom end and at a top end. The dry weight of the test sample and glass plate was determined, and a rectangular dish 30 cm by 19 cm by 4 cm was filled with one cm of test fluid. The absorbent sample was placed on the glass plate with one edge positioned at the bottom glass plate edge that had been calibrated with inch marks. The glass plate was then lowered into the dish such that its bottom edge formed a 10-degree angle with the bottom of the dish. The time required for the liquid to wick up to 1-, 2-, 3-, and 4-inch marks was observed, and the time required to reach the 4-inch mark was recorded as the wicking time. When the liquid reached the 4-inch mark, or 5 minutes had elapsed, the plate and sample were removed and then the weight was determined. The amount of liquid wicked was calculated by subtracting the weight of the glass plate and weight of the dry sample.

Total capacity was determined using a procedure similar to that of the wicking test, but the glass plate and sample were reversed. The plate was again placed at a 10-degree angle, but this time with the wet sample at the top of the plate. A synthetic urine colored with food color was slowly dripped onto the wet sample until it was filled to capacity. Capacity was reached when the liquid saturated the sample and "breaks" from the pad, that is, when the liquid began flowing away from the bottom edge of the pad and ran down the inclined plate. The plate and glass were removed and weighed. The total liquid capacity was calculated by subtracting the weight of the plate and the dry sample. Liquid capacity of sample per gram dry weight was calculated by dividing liquid capacity by sample dry weight.

To determine capacity under load, the wet sample was transferred from the glass plate to the center of a screen with 16 holes per square inch. A metal disk was placed on the sample and a weight as specified in Table IX was placed on top of the disk to apply a load to the saturated sample. The sample was allowed to drain for three minutes and its weight was then determined. The capacity under load was calculated by subtracting the weight of the dry sample.

Pad comparison and wetting tests are shown in Table IX for a variety of crosslinking agents to illustrate the superior wicking properties and total capacity of some of the crosslinkers of the present invention.

TABLE IX

PAD COMPRESSION AND WETTING TESTS WITH VARIOUS CROSSLINKERS

| Crosslinker | Total Capacity (g/g) | Wet Bulk (cc/g) | Dry Pad Density (g/cc) | Wicking Capacity (g/g) | Wicking Time (sec) | Press Force (°C.) | Press Temp (°C.) |
|---|---|---|---|---|---|---|---|
| NB316--None | 9.6 | 8.6 | 0.25 | 7.5 | 40 | 12000 | 22 |
| HBA (New Bern) | 10.6 | 9.3 | 0.24 | 8.8 | 32 | 34000 | 90 |
| Glutaraldehyde, unw. (Market Pulp R&D) | 12.9 | 11.7 | 0.28 | 9.7 | 27 | 7000 | 90 |
| Glyoxal + DEG | 8.2 | 7.8 | 0.28 | 6.3 | 44 | 8000 | 90 |
| N-Sulfatosuccinimide | 16.4 | 15.0 | 0.17 | 12.9 | 25 | 30000 | 85–90 |
| Glutaraldehyde (wet X-link) | 15.8 | 13.3 | 0.34 | 10.6 | 25 | 10000 | 90 |
| 1,3-Dichloro-2-propanol (wet) | 15.2 | 12.2 | 0.38 | 12.2 | 36 | 6000 | 94–96 |
| Methylene-bis-acrylamide (wet) | 18.5 | 15.9 | 0.23 | 15.4 | 25 | 5000 | 90 |
| Sulfonyldiethanol (wet) | 11.0 | 9.0 | 0.26 | 9.6 | 34 | 6000 | 90 |
| Glyoxal + 2-Imidazolidone | 13.2 | 11.8 | 0.22 | 10.2 | 25 | 35000 | 110* |
| BTCA (30 min oven cure) | 8.4 | 7.7 | 0.24 | 6.6 | 32 | 35000 | 160** |
| Sodium Periodate/NB316 | 16.1 | 14.3 | 0.20 | 9.9 | 19 | 6000 | 104 |
| Sodium Periodate/NB316 + Al(SO$_4$)$_3$ | 13.4 | 11.5 | 0.25 | 8.2 | 22 | 26000 | 104 |

*Pressed twice
**Pressed 4–5 times

Figure 11:
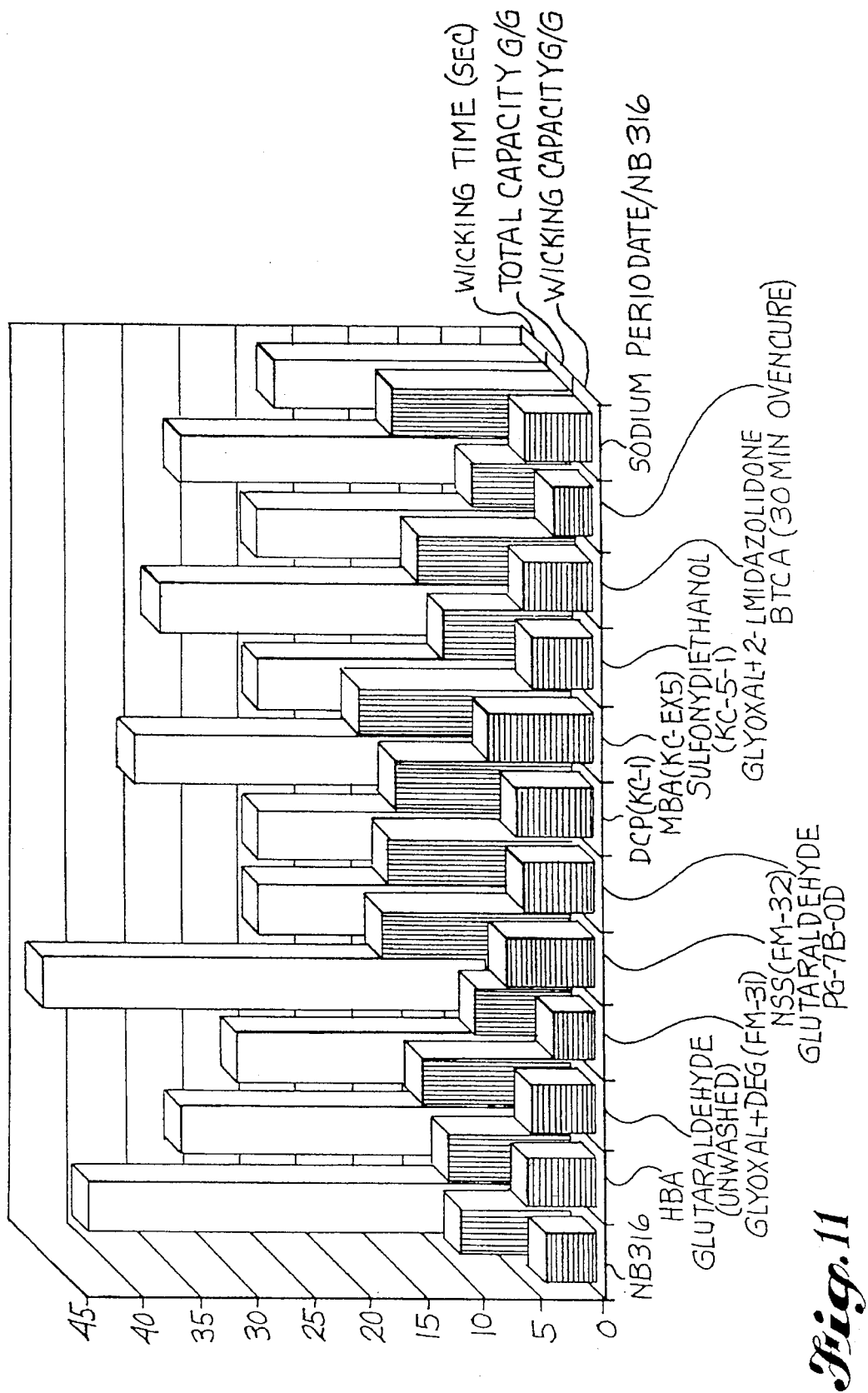
FIG. 11 is a graph Showing properties of an absorbent material crosslinked with a variety of crosslinking agents.

These results are illustrated in FIG. 11, which shows that sodium periodate, glyoxal/2-Imidazolidone and N-sulfatosuccinimide (NSS) have wicking times that are significantly decreased over previous crosslinkers such as HBA (urea formaldehyde) and BTCA (butanetetracarboxylic acid). Glyoxal/2-Imidazolidone, sodium periodate and glutaraldehyde crosslinked samples showed enhanced total capacity.

Using the Crosslinking Agents

The crosslinking agents of the present invention can be used for many wood product applications. The agents may be used, for example, to strengthen linerboard or wood. The following Examples illustrate several uses of the crosslinkers of the present invention.

EXAMPLE VII

Crosslinking Fluff Pulp

A pulp sheet is impregnated with an aqueous solution of crosslinking agent and catalyst. The concentrations of crosslinking agent and catalyst are such that the quantity of water used is preferably at least 40% of the weight of the pulp to ensure good wetting and distribution in the fibers, and such that the amount of crosslinking agent applied is equal to 1–20% of the weight of the pulp. The pulp sheet is then fiberized, dried and cured at a temperature high enough to cause the crosslinking reaction to occur and for a length of time sufficient to allow the crosslinking reaction to go to completion.

EXAMPLE VIII

Crosslinking and Stiffening Kraft Liner Board

Liner board is impregnated with an aqueous solution of crosslinking agent and catalyst. The concentrations of crosslinking agent and catalyst are such that the quantity of water used is at least 30% of the weight of the liner board to ensure good wetting and distribution in the liner board, and such that the amount of crosslinking agent applied is equal to 1–20% of the weight of the liner board. The liner board is then dried and cured at a temperature high enough to cause the crosslinking reaction to occur and for a length of time sufficient to allow the crosslinking reaction to go to completion.

EXAMPLE IX

Crosslinking Wood to Increase Dimensional Stability

Lumber is impregnated with an aqueous solution of crosslinking agent and catalyst using a standard vacuum/pressure process. The concentration of crosslinking agent is such that the quantity of crosslinking agent remaining in the wood after impregnation is equal to 1–20% of the weight of the wood. The wood is then air dried or kiln dried followed by heating to a temperature high enough to cause the crosslinking reaction to occur and for a length of time sufficient to allow the crosslinking reaction to go to completion. One particular application, which is given for purposes of illustration and is not meant to be limiting, is provided in this Example. A process is shown in this Example for producing individualized, intrafiber crosslinked cellulose fibers that are useful in manufacturing products such as paper towels, baby diapers and sanitary products. This process is more fully disclosed in copending U.S. patent application Ser. No. 07/607,312.

Overall System

The apparatus 10 (FIG. 1) of the present invention comprises a conveying device 12 for transporting a mat 14 of cellulose fibers or other fibers through a fiber treatment zone 16; an applicator 18 for applying a treatment substance such as a crosslinking substance from a source 19 thereof to the mat 14 at the fiber treatment zone 16; a novel type of fiberizer 20 for completely separating the individual cellulose fibers comprising the mat 14 to form a fiber output comprising substantially unbroken cellulose fibers substantially without nits or knots; and a dryer 22 coupled to the fiberizer for flash-evaporating residual moisture from the fiber output and for curing the crosslinking substance, thereby forming dried and cured cellulose fibers. The apparatus 10 of the present invention has been observed to consistently produce fibers with a nit level of less than three, which is substantially lower than obtainable using any apparatus presently known in the art.

Raw Materials

As used herein, a "mat" denotes any non-woven sheetlike structure comprising cellulose fibers or other fibers that are not covalently bonded together. The fibers may be obtained from wood pulp or other source including cotton "rag", hemp, grasses, cane, husks, cornstalks, or any other suitable source of cellulose fiber that can be laid into a sheet.

Preferably, the mat 14 includes a debonding agent which can be applied after formation of the mat 14 or added to cellulose fibers before forming the mat therefrom. For example, with mats comprising pulp fibers, the debonding agent can be added to wet pulp before the mat is laid using conventional papermaking machinery. Debonding agents tend to minimize interfiber bonds between fibers of the mat. A fair, but nonexhaustive, sampling of debonding agents is disclosed in U.S. Pat. Nos. 3,395,708 and 3,544,862 to Hervey, et al.; 4,144,122 to Emanuelsson, et al.; 3,677,886 to Forssblad, et al.; 4,351,699 to Osborne III; 4,476,323 to Hellsten, et al.; and 4,303,471 to Laursen, all of which are herein incorporated by reference. Any suitable debonding agents may be used, such as preferably Berocell 584 from Berol Chemicals, Incorporated of Metairie, La. in a 0.25% weight of debonder to weight of fiber. However, use of a debonding agent is not required for complete fiberization using the present apparatus.

The mat 14 of cellulose fibers is preferably in an extended sheet form stored in the form of a roll 24 until use. While the mat 14 can also be one of a number of baled sheets (not shown) of discrete size, rolls 24 are generally more economically adaptable to a continuous process. The cellulose fibers in the mat 14 should be in a non-woven configuration produced by a pulping process or the like, such as in a paper mill, and can be bleached or unbleached. The mat 14 can have any of a wide variety of basis weights. For simplicity, FIG. 1 shows a roll 24 as the source of each mat 14, but it is to be understood that the mat 14 can be supplied in any form amenable for storing sheet-like structures. Also, the mat may be obtained directly from the headbox of paper making equipment or otherwise formed in any suitable manner.

It is normally not necessary that the cellulose fibers comprising the mat 14 be completely dry. Since cellulose is a hydrophilic substance, molecules thereof will typically have a certain level of residual moisture, even after air drying. The level of residual moisture is generally 10% w/w or less, which is not detectable as "wetness."

FIG. 1 also shows that more than one supply, such as multiple rolls 24, of the mat 14 of cellulosic fibers can be simultaneously processed using the present invention. For simplicity, FIG. 1 shows two rolls 24 being processed, but it is to be understood that even more supplies of cellulosic fibers can be simultaneously processed, depending upon the capacity of the equipment, particularly the fiberizer 20. As discussed herein below, the preferred embodiment of the fiberizer 20 can fiberize up to six mats at one time.

At the fiber treatment zone 16, sprayers or other applicators 18 apply chemicals such as crosslinking agents to the mat. Typically, chemicals are applied uniformly to both sides of the mat. In one particular embodiment of the applicator in which a pair of opposing sprayers 18 are positioned adjacent each face of mat 14 to spray crosslinking agent at the mat and saturate it with the crosslinking agent. The wetted mat passes between a pair of impregnation rollers 28 which assist in distributing the chemicals uniformly through the mat. Rollers 28 cooperatively apply light pressure on the mat (for example, 1–2 psi) to force crosslinking agents uniformly into the interior of the mat across its width. The rollers 28 form a seal with the mat such that the crosslinking agent can form a puddle at the nip. This seal helps prevent the liquid crosslinking agent from falling into the inlet 34*a* of the fiberizer 32 that is positioned vertically below the flooded nip. Other applicators may also, of course, be used. Examples of other applicators include size presses, nip presses, blade applicator systems and foam applicators.

Each mat 14 is urged by the first and second pair of rollers 26, 28 through the fiber treatment zone 16 where the mat 14 is impregnated With a liquid crosslinking substance. The crosslinking substance is preferably applied to one or both surfaces of the mat using any of a variety of methods known in the art useful for such a purpose, such as spraying, rolling, dipping, or an analogous method. Spraying has the advantage of consistent and rapid full coverage of a planar surface such as a mat at a controllable rate, especially when the spray is applied to a surface moving past a spray nozzle or analogous applicator at a fixed rate. Roller applicators have also proven to be reliable and effective in such applications as paper coating and the like and would therefore be effective for applying the crosslinking substance in the present instance. Combinations of spray and roller applicators can also be employed.

The crosslinking substance is typically applied in an amount ranging from about 2 kg to about 200 kg chemical per ton of cellulose fiber and preferably about 20 kg to about 100 kg chemical per ton of cellulose fiber.

The rollers 28 can be positioned relative to each other to have a defined gap therebetween so as to enable them to impart a controlled squeeze action to the impregnated mat as it departs the fiber treatment zone 16. As mentioned above, such squeezing action facilitates complete and uniform penetration of the crosslinking substance throughout the thickness dimension of the mat. The squeezing action also helps to regulate the degree of saturation ("loading level") of the mat 14 with the crosslinking substance.

The crosslinking substance is a liquid solution containing any of a variety of crosslinking solutes known in the art. If required, the crosslinking substance can include a catalyst to accelerate the bonding reactions between molecules of the crosslinking substance and cellulose molecules. However, many if not most crosslinking substances do not require a catalyst.

In FIG. 1, the crosslinking substance applied to the mat 14 is obtained from a supply 19 thereof, such as a tank or analogous vessel. It is also possible for the supply 19 of crosslinking substance to be continuously produced on-line to prevent pre-cure of the crosslinking substance that may occur over time if it were stored in a large vessel. On-line production of the crosslinking substance is particularly advantageous when it contains a catalyst. Alternatively, for example, a batch of the crosslinking substance can be prepared fresh each day, so long as no significant deterioration of the solution will occur during the period in which the batch is consumed.

Crosslinked cellulose fibers are individual fibers each comprising multiple cellulose molecules where at least a portion of the hydroxyl groups on the cellulose molecules have been covalently bonded to hydroxyl groups on neighboring cellulose molecules in the same fiber via crosslinking reactions with extraneously added chemical reagents termed "crosslinking substances" or "crosslinking agents". Suitable crosslinking agents are generally of the bifunctional type which create covalently bonded "bridges" between said neighboring hydroxyl groups.

Crosslinked cellulose fibers have particular applicability not only in wrinkle-resistant fabrics but also in materials derived from wood pulp having one or more desirable characteristics such as high loft, low density, high water absorbency, resiliency, and light weight. As a result, crosslinked cellulose fibers are candidates for use in absorbent structures found in disposable products such as diapers and pads. They are also useful for paper toweling, wiping cloths, filters, and other similar uses.

Despite their desirable qualities, crosslinked cellulose fibers have previously enjoyed limited success as a raw material. A principal reason for this is because the most convenient way for a manufacturer to crosslink cellulose fibers is by application of the crosslinking agent to a cellulosic fibrous sheet or mat which must be subsequently fiberized (all the constituent fibers of the sheet or mat separated from one another) before the fibers can be subjected to a step in which the crosslinking agent is cured. If any curing occurs before the fibers are completely separated, interfiber bonding can occur which would make any subsequent attempt at complete fiberization virtually impossible.

Crosslinked cellulose fibers when used in many products cannot have excessive amounts of certain defects known in the art as "knots" or "nits". Knots are agglomerations of fibers remaining after an incomplete fiberization of a cellulosic fibrous sheet. Nits may be defined as hard, dense agglomerations of fibers held together by the crosslinking substance due to the ability of crosslinking agents to covalently bond individual fibers together (interfiber bonding). Nits are generally regarded in the art as having a surface area of about 0.04 mm$^2$ to about 2.00 mm$^2$. A nit usually has a density greater than 0.8 g/cm$^3$, where a density of about 1.1 g/cm$^3$ is typical. The fibers comprising a nit virtually cannot be separated from one another in a conventional fiberizing device. As a result, these recalcitrant particles become incorporated into the final product where they can cause substantial degradation of product aesthetic or functional quality. For example, nits can substantially reduce the absorbency, resiliency, and lot of an absorbent product. For aesthetically sensitive products, such as high quality paper, a "nit level" of three or less (two or fewer nits per 6-inch diameter test "handsheet"; see Example 1) is generally regarded as a maximally acceptable number of nits. Knots can also seriously degrade product appearance. Also, as an example of the effect of these particles on product performance, filters made using crosslinked fibers containing any nits and knots would in many cases be incapable of performing to specifications.

Conveying Device

Referring further to FIG. 1, each mat 14 of cellulosic fibers is conveyed by a conveying device 12, which can comprise, for example, a conveyor belt or a series of driven rollers with the mat positioned therebetween. The conveying device 12 carries the mats through the fiber treatment zone 16. FIG. 1 also shows a further portion of one type of conveying device comprised of a first pair of rollers 26 and a second pair of rollers 28 for each mat 14. The first and second pair of rollers 26, 28 are particularly effective for urging the corresponding mat at a substantially constant and controlled rate of speed.

Fiberizer

The subsystem following the fiber treatment zone is a fiberizer 20 which serves to comminute one or more mats 30 impregnated with the crosslinking substance into individual substantially unbroken cellulose fibers comprising a fiber output. The fiberizer 20 performs its task on one or more mats, which are preferably still moist (but which may be dry) from application of the crosslinking agent. In this case, the wet sheets are delivered directly and immediately to the fiberizer by the conveyor 12 without aging or other significant delays. As detailed below, the preferred embodiment of the fiberizer 20 is designed to minimize interfiber bonding and the formation of nits therein. Also, the preferred embodiment of the fiberizer 20 thoroughly fiberizes each impregnated mat 30, thereby virtually eliminating residual knots.

The preferred embodiment of the fiberizer 20 comprises an attrition device 32 as detailed hereinbelow and in copending U.S. patent application Ser. No 07/607,312 entitled "Fiberizing Apparatus" filed on Oct. 31, 1990, which is incorporated herein by reference. The attrition device 32 preferably can simultaneously fiberize a plurality of impregnated mats 30 and has a separate mat inlet 34a, 34b for receiving each corresponding impregnated mat.

Figure 2:
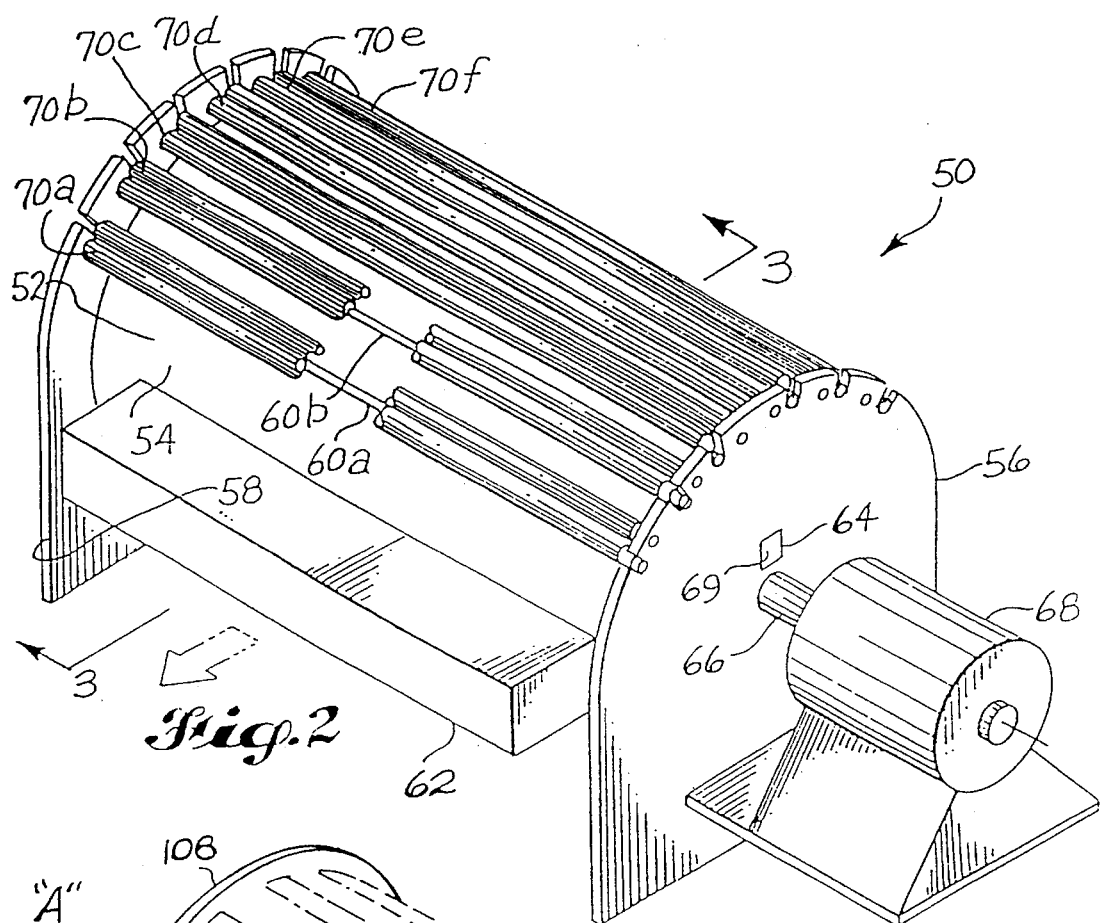
FIG. 2 is an isometric external view of a preferred embodiment of an attrition device, where certain details of the mat feeder assemblies have been omitted for clarity.

The exterior of a preferred embodiment of the attrition device 50 is shown in FIG. 2, which comprises an elongated cylinder-shaped housing 52 having an exterior surface 54. A first end panel 56 is located on one end of the housing 52 and a second end panel 58 is located at the other end of the housing 52. Multiple mat inlets (two of which 60a, 60b are shown) defined by the housing are located radially in an arc comprising a portion of the circumference of the housing 52, where each mat inlet is dedicated to feeding a separate mat into the attrition device 50. An outlet chute 62 extends from the housing 52. Each end panel 56, 58 defines a central orifice 64 through which coaxially extends a corresponding rotor shaft end 66 rotatable relative to the housing 52. One rotor shaft end 66 is coupled to a drive motor 68 serving to impart rotational motion thereto.

An air flow port 69 is provided through each end panel 56, 58. As a downstream blower 160 (discussed below) coupled to outlet 62 is operated, air is drawn in through openings 69, and around the ends of the rotor 100 (discussed below in connection with FIG. 4) to assist in minimizing the accumulations of fiber at such locations. Although variable, air typically flows at a rate of about 50 m$^3$/min through each of the openings 69. Also, a conduit (not shown) is typically included and coupled to wall 52 delivering water or other cleaning fluid to the interior of the housing through plural nozzle openings to clean any fiber accumulations from the attrition device. A liquid cleaning operation is typically accomplished by directing water toward the rotors in a direction somewhat counter to the direction of the normal rotor rotation as the rotor is rotated in this direction. Cleaning may be periodically performed, such as once every sixteen hours of operation of the attrition device, depending in part upon the volume of fiber being processed. By cleaning fiber accumulations in this manner, the accumulations do not end up in the finished product where they may comprise bonded nits.

Each mat inlet includes a feeder assembly, such as assemblies 70a–70f shown partially in FIG. 2, each mounted exteriorly relative to the cylindrical housing 52 at a location adjacent the corresponding mat inlet. A representative feeder assembly (such as 70d in FIG. 2) is shown in more detail in the transverse sectional view of FIG. 3. Each feeder assembly 70 is comprised of a first feed or seal roller 72 and a second feed or seal roller 74 extending longitudinally between the first and second end panels 56, 68 (FIG. 2). Also extending longitudinally between the first and second end panels 56, 58 are corresponding support angles or brackets (such as 76a and 76b in FIG. 3) and wedge-shaped alignment or mounting bars (such as 78a and 78b in FIG. 3). Since FIG. 3 only depicts one feeder assembly 70d, angles 76a and 76b correspond to the feeder assembly 70d. The first and second seal rollers 72, 74 extend longitudinally in a direction substantially parallel to, and have a length substantially equal to, the corresponding mat inlet 60a situated between a leg 80 of the angle bracket 76a and a leg 82 of the angle bracket 76b. The seal rollers 72, 74 are rotatably mounted for rotation about their respective longitudinal axes 84, 86 at locations equidistant from the mat inlet 60a. The distance D, from a plane through the axes of seal rollers 72, 74 to the effective rotor surface 144 swept by the hammers of the rotor 100 (FIG. 4) is preferably from about one-half inch to no more than about four inches when wet sheets are being fed to the rotor 100. This minimizes the possibility of plugging of the opening 60a as the sheets are being delivered thereto.

In one specifically preferred design, each seal roller has a central shaft and an outer roll. The ends of the central shaft of each seal roller 74 are coupled by a respective bearing to the end plates 56, 58. In addition, the ends of the central shaft of the seal rollers 72 are supported for rotation by a bracket (one being shown as 87 in FIG. 3). Typically the seal rollers are of a rigid material, such as steel, with the seal roller 74 being mounted at a fixed location. The ends of the shaft of the seal roller 72 are positioned within respective recesses 85 in the respective brackets 87. The bracket 87 may be pivotally coupled to the housing for pivoting in the direction of arrow 91 upon removal of a bolt or other stop 89. When bracket 87 is shifted upwardly in FIG. 3, the seal roller 72 may be removed for repair and or cleaning and to provide access to seal roller 74. Pneumatic cylinders, not shown, typically apply a load of from 5 psi to 80 psi to the respective ends of the shaft of the seal roller 72 to bias the seal rollers together. This pressure is typically relieved to allow the feeding of a sheet between the seal rollers and is then reinstated during normal operation of the attrition device. At least one of the seal rollers, such as roller 74, is rotatably driven via a motor (not shown) at a controlled angular velocity to advance a mat (not shown) situated between the first and second rollers 72, 74. Roller 74 may, for example, be driven in the direction of arrow 93 at a predetermined mat feed rate through the mat inlet 60a.

A first guide 88 and a second guide 90 are also mounted to the corresponding mounting brackets 76a and 76b, respectively. Each of the guides 88, 90 extend longitudinally in a direction substantially parallel to the corresponding seal rollers 72, 74, respectively. Each guide 88, 90 is typically constructed of a rigid material and includes an outer edge 92, 94, respectively, adjacent to, but spaced from the surface of the corresponding seal roller 72, 74, respectively, along the full length of the roller. The guides 88, 90 thereby serve to substantially prevent air from passing past the guides and to the corresponding mat inlet 60a. Therefore, substantially all of the air drawn into the attrition device passes through the openings 69 (as previously explained).

The fiber mat passing through inlet 60a passes an optional nose bar 95 and is delivered against the rotor 100 traversing the effective rotor surface 144 (FIG. 3). The gap between the inlet 60a and the effective rotor surface is typically no more than about one-fourth to one inch.

Figure 4:
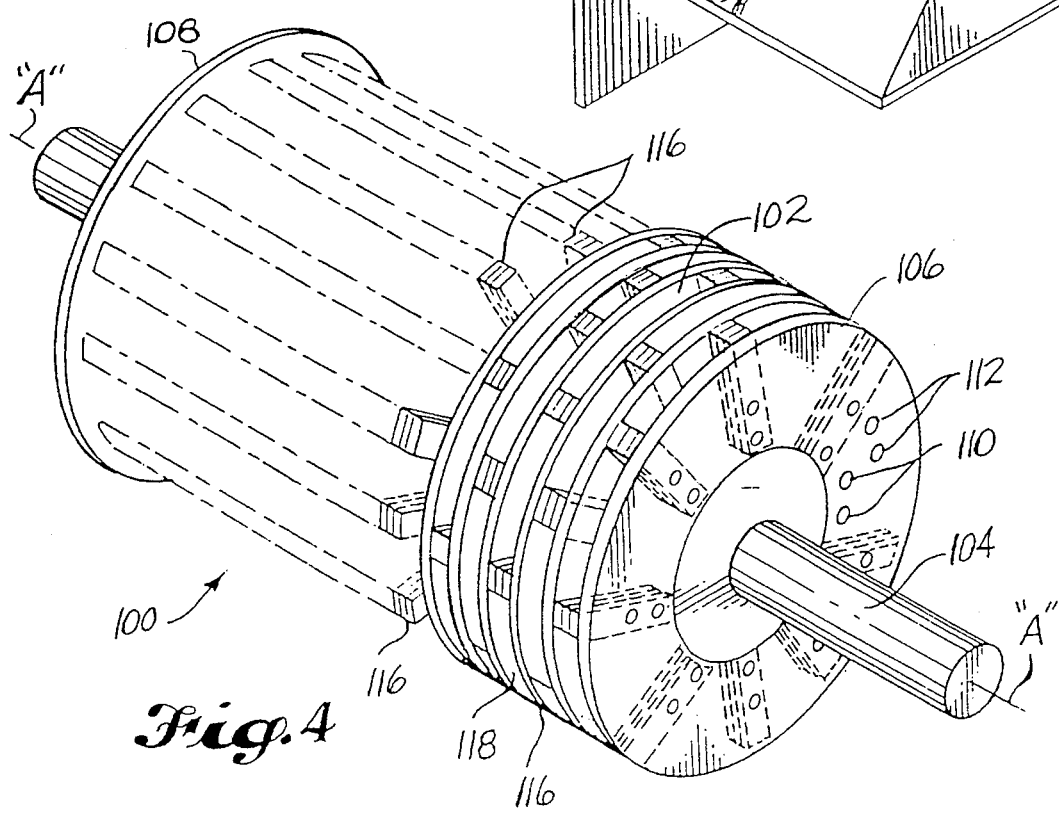
FIG. 4 is an isometric view of the rotor of the attrition device of FIG. 2.

FIG. 4 shows a rotor 100 of the type coaxially mounted inside the attrition device housing 52 (FIG. 1). The rotor 100 comprises a plurality of substantially annular spacer or hammer mounting plates 102 mounted to the rotor shaft 104. The plates 102 extend radially outwardly from the longitudinal axis "A" of the rotor shaft 104 and are parallel to one another. The rotor 100 also has a first rotor end plate 106 and a second rotor end plate 108, each substantially annular in shape and oriented parallel to the mounting plates 102. The first and second rotor end plates 106, 108 are mounted coaxially to the rotor shaft 104 and have a diameter sufficiently large such that only a narrow gap (e.g. one-sixteenth to one-half inch) is left between the inner surface of the cylindrical housing (not shown in FIG. 4) and the perimeter of the first and second end plates 106, 108. The illustrated plates 106, 108 extend radially outwardly beyond the distal ends of hammers 116 to minimize the possible accumulation of fibers adjacent to the end plates.

Attached to and extending between the first and second end plates are plural inner mounting rods 110 and an identical number of outer mounting rods 112 oriented parallel to the longitudinal axis "A" of the rotor shaft 104. The inner and outer mounting rods 110, 112 are secured to the first and second rotor end plates 106, 108. As shown clearly in FIG. 4, the mounting rods 110, 112 are arranged as plural equiangularly spaced pairs. Each pair comprises a single inner mounting rod 110 and a radially outwardly positioned single outer mounting rod 112. A typical rotor 100 has sixteen such pairs of rods arranged radially about the rotor axis "A".

Each pair of mounting rods 110, 112 has mounted thereto plural groups of hammer plates, each group comprising a hammer assembly 116. Each such hammer assembly 116 is located either between adjacent mounting plates 102 or between a spacing plate 102 and an adjacent rotor end plate 106, 108. However, each hammer assembly 116 is spaced from an adjacent hammer assembly 116, by an empty space 118 large enough to accommodate another hammer assembly. As a result, on a rotor 100 with twenty-seven mounting plates 102 and two rotor end plates 106, 108, for example, the maximal number of hammer assemblies 116 held by a given pair of mounting rods 110, 112 is fourteen.

A representative flat hammer plate 130 of assembly 116 is depicted in FIG. 5, wherein each hammer plate 130 has a proximal end 132 positioned toward the rotor axis (not shown) and a distal end 134 positioned radially outward relative to the rotor axis. The hammer plate 130 also defines two mounting holes 136a, 136b for attaching the hammer 130 to an associated pair of mounting rods 110, 112 (not shown in FIG. 5). The distal end surface 134 of the hammer plate has a trailing edge 138 and a leading edge 140, wherein the leading edge 140 extends radially outward relative to the rotor axis beyond the trailing edge 138. The distal end 134 is cut at a five degree angle relative to a line 142 parallel to the proximal edge 132. The direction of rotation of the rotor is indicated by an arrow 145 in FIG. 5.

As shown in FIG. 6, each illustrated hammer assembly 116 comprises plural planar plate-like hammers 130 (three being shown in this figure). These plates are typically spaced apart by spacers (not shown). Each of said hammer assemblies 116 located between adjacent mounting plates 102 (only one plate 102 being shown in this figure) also includes a left-angled hammer 146 and a right-angled hammer 148 each having a lip 150a, 150b, respectively, extending transversely in an opposing direction relative to each other. The width dimension 152 of the lip of each angled hammer is typically equal to or slightly less than half the thickness dimension of a mounting plate 102. Also, each of the hammer assemblies 116 located between a plate 102 and a rotor end plate replaces one of the L-shaped hammers with a flat hammer plate adjacent to the end plate. Other hammer configurations and arrangements may be used. However, a preferred hammer arrangement minimizes any gaps in the surface swept by hammer elements to preferably no more than one-fourth of an inch.

The illustrated embodiment 50 of the attrition device is operated by driving the rotor 100 at a high angular velocity while feeding one or more impregnated mats through one or more corresponding mat inputs. The mat is urged at a controlled linear velocity into the corresponding mat input slot 60 by the controlled rotation of the feed rollers 72, 74. As the impregnated mat enters a mat inlet, it is repeatedly impacted by the distal end surface and in particular, the leading edge of the hammer plates, which effectively and completely comminutes the mat into its individual constituent fibers, substantially free of knots and nits.

The preferred embodiment 50 of the attrition device as described hereinabove is particularly effective in simultaneously fiberizing one or more separate mats (up to six) to form a volume of individualized cellulose fibers having a nit level substantially lower than levels achievable with existing attrition devices such as hammermills. This is believed to be due to the fact that the present attrition device lacks hot spots and dead spaces, wherein fibers can accumulate, found in conventional hammermills or other attrition devices currently used in the art.

Referring further to FIG. 1, a first conveyor fan 160 of conventional design can be utilized for propelling the fibers from the outlet 62 of the attrition device 32 through a conduit 162.

An optional component of the fiberizer 20 is a first cyclone 164 or similar apparatus known in the art, utilized in a conventional manner to concentrate the fibers passing out of the outlet 62 of the attrition device 32. The first cyclone 164 receives the fibers through the conduit 162 coupled thereto.

Excess air can be recovered at the top 166 of the first cyclone 164 and recycled as required through a conduit to a location upstream of the first conveyor fan 160 (if used). Such additional air can be beneficial for easing the transfer of the fibers through the first conveyor fan 160.

A disk refiner 168 is another optional component of the fiberizer 20 which can be employed to effect additional separation of fibers (removal of knots) if required. The disk refiner 168 is of a type known in the art and comprises a disk refiner inlet 170 and a disk refiner outlet 172. A representative disk refiner 168 is type DM36 manufactured by Sprout-Bauer, Incorporated of Muncie, Pa. If the disk refiner 168 is used, the inlet 170 thereof is coupled via a conduit 174 to an outlet 176 of the first cyclone 164.

A second conveyor fan 178 may optionally be utilized to urge propagation of the fibers through a conduit 180 downstream of the disk refiner 168. Excess air can be recovered from the top 166 of the first cyclone 164 and routed via a conduit 181 to a tee 182 just upstream of the second conveyor fan 178.

Another optional component of the fiberizer 20 is a fluff generator 190 which receives the fibers from the optional second conveyor fan 178 through a conduit 184. The fluff generator is described in detail below and in copending U.S. patent application Ser. No. 07/607,157 entitled "Multi Pin Rotor Fiber Fluff Generator" filed on Oct. 31, 1990, incorporated herein by reference.

Referring now to FIG. 7, a preferred embodiment of the fluff generator 190 comprises a housing 192 shaped in the form of three contiguous, partially intersecting cylinders, including a first housing portion 194 opening into a second (or middle) housing portion 196, which opens into a third housing portion 198. Each housing portion 194, 196, 198 has a longitudinal coplanar axis A1, A2, A3, respectively. The housing 192 has an inlet 200 permitting delivery (arrow 202) of fibers to the first housing portion 194, and an outlet 204 conducting fluffed fibers away (arrow 206) from the third housing portion 198.

Figure 8:
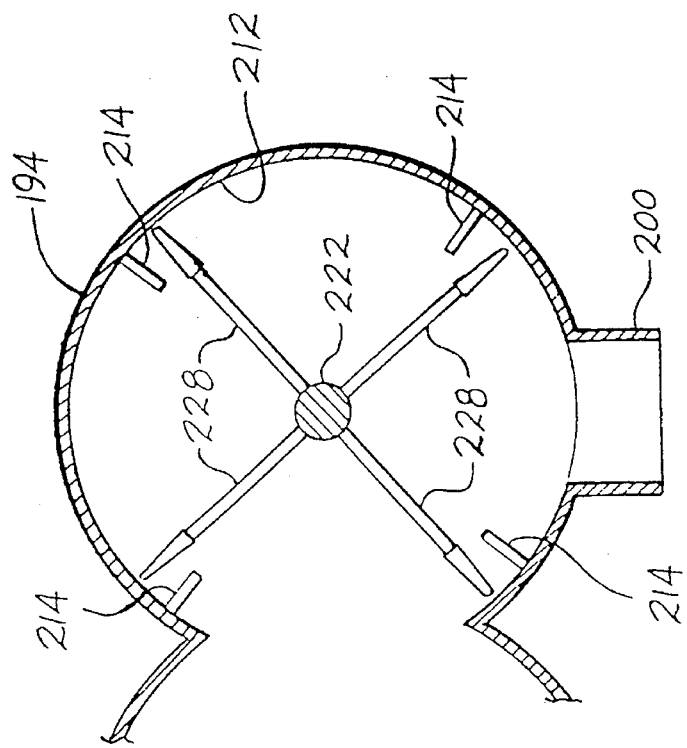
FIG. 8 is a transverse sectional view through a housing portion and rotor of the fluff generator of FIG. 7.
Figure 10:
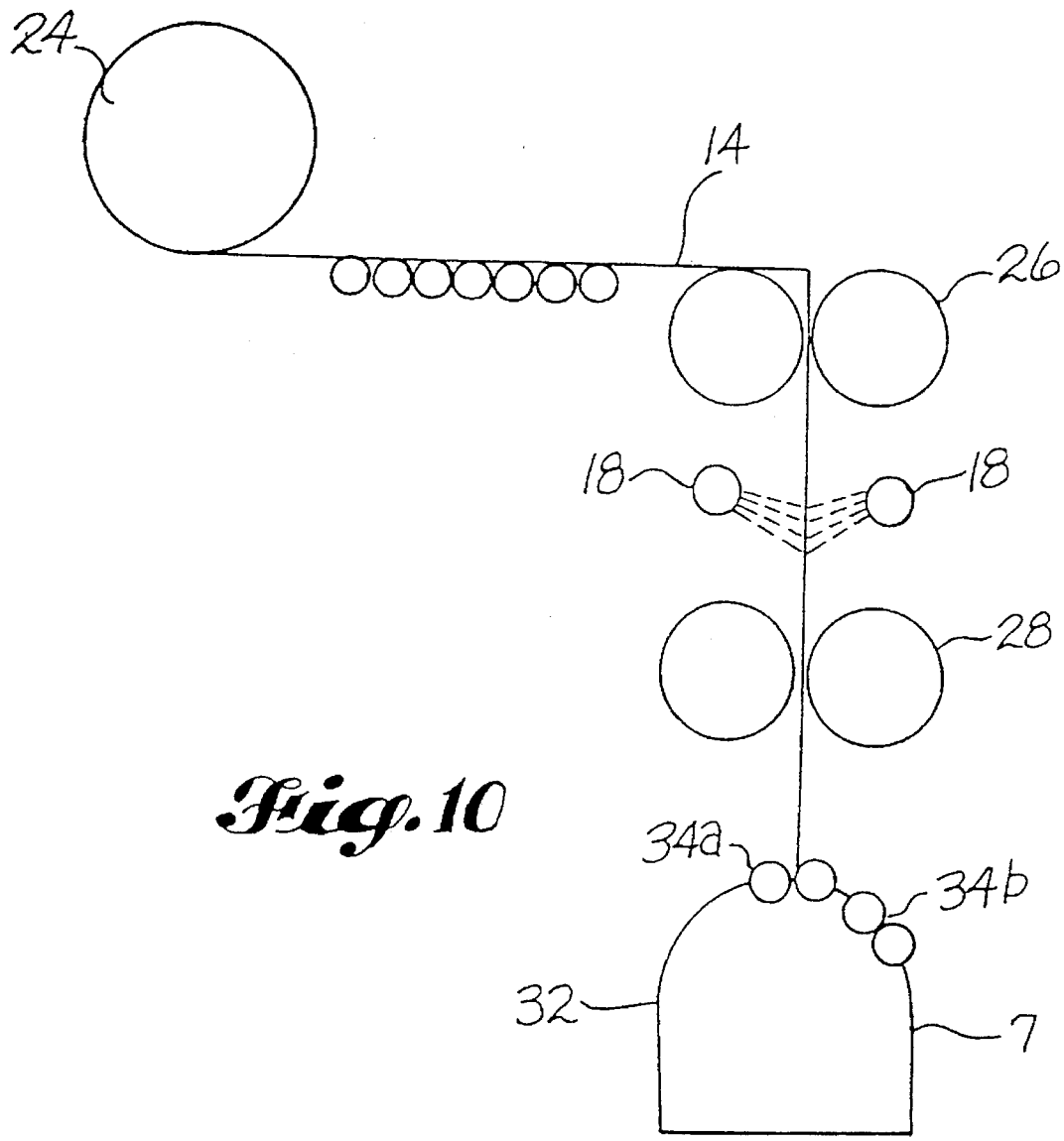
FIG. 10 is an enlarged view of the crosslinking applicator portion of the diagram of FIG. 1.

As shown in FIG. 8, showing a transverse sectional view of the first housing portion 194, the interior surfaces 212 of each of the first, second, and third housing portions have affixed thereto multiple stator pins 214 radially pointing toward the respective axis of the housing portion. The pins 214 are grouped in longitudinally extended rows along lines parallel to the respective housing portion axis.

Figure 9:
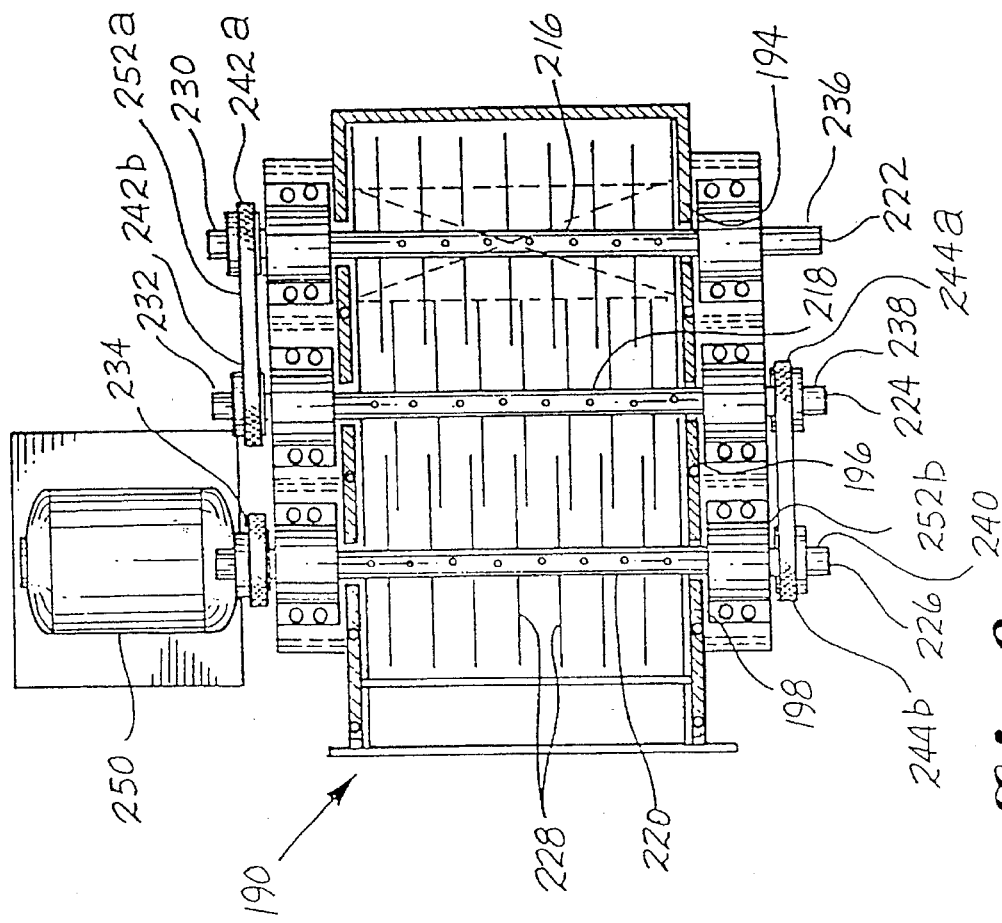
FIG. 9 is a plan sectional view of the fluff generator of FIG. 7.

Each of the first, second, and third housing portions 194, 196, 198, respectively, is in surrounding relationship to a first rotor 216, a second rotor 218, and a third rotor 220, respectively, as shown in FIG. 9. Each rotor 216, 218, 220 has a corresponding rotor shaft 222, 224, 226, coaxial with the axis A1, A2, A3 of the respective housing portion. As shown in FIG. 8 (showing a transverse sectional view of the first housing portion 194 only, but applicable to illustrate similar details inside the second housing portion 196 and third housing portion 198) and FIG. 9, to the shaft 222 of the rotor 216 are mounted four longitudinally extended rows of plural rotor pins 228, where each row of rotor pins 228 is equiangularly spaced in a radial manner around the corresponding rotor shaft 222. The rotor pins 228 radially extend from the shaft 222 nearly to the inside surface 212 of the corresponding housing portion 194 but are positioned on the rotor shaft 222 such that they will pass between longitudinally adjacent stator pins 214 when the rotor 216 is rotating about its axis. Rotor shafts 224 and 226 are similarly equipped with rotor pins 228.

As shown in FIG. 9, each rotor shaft 222, 224, 226 has a first end 230, 232, 234, respectively, and a second end, 236, 238, 240, respectively, each extending through and journaled in the corresponding housing portion 194, 196, 198, respectively. The first and second ends of each rotor shaft extend outside the corresponding housing portion. A pulley 242a, 242b is attached to each of the first ends 230, 232, respectively, of the first and second rotor shafts 222, 224, respectively. Likewise, a pulley 244a, 244b is attached to the second ends 238, 240, respectively, of the second and third rotor shafts 224, 226, respectively. The first end 234 of the third rotor shaft is rotatably coupled directly or indirectly to a drive motor 250. Each set of pulleys is coupled by a drive belt 252a, 252b ensuring that, when the drive motor 250 rotates the third rotor 220, the second and first rotors 218, 216, respectively, synchronously rotate in the same rotational direction as the third rotor 220.

The fluff generator 190 is operated by synchronously driving the rotors 216, 218, 220 at a high rotational speed and conducting fibers 202 (FIG. 7) from their disk refiner 168 (FIG. 1), where the velocity of said fibers is increased via the second conveyor fan 178, into the inlet 200 of the fluff generator 190. The fibers are conducted sequentially through the first, second, and third housing portions 194, 196, 198, respectively, and exit 206 the fluff generator 190 through the outlet 204. As the fibers pass through the housing 192 of the fluff generator 190, they encounter strong agitation and turbulence generated by the groups of rotor pins 228 on each of the three rapidly rotating rotors 216, 218, 220 passing by the stationary stator pins 214. By encountering such turbulence and agitation, any knots remaining in the fibers are comminuted to form a fiber output containing virtually no knots.

As used herein, the "fiber output" is the mass of thoroughly individualized fibers exiting the fiberizer 20 and passing to the dryer 22.

As discussed hereinabove, the disk refiner 168 and fluff generator 190 are optional components of the present apparatus 10. In most cases, the attrition device 32 alone is adequate for completely fiberizing plural mats. However, in cases where the mats are unusually bulky, the disk refiner 168 and fluff generator 190 can be employed, particularly to ensure the absence of knots in the fiber output.

Dryer

Referring further to FIG. 1, a preferred embodiment of the present apparatus 10 includes a dryer 22 which is utilized to perform two sequential functions: remove residual moisture from the fibers and cure the crosslinking agent. Preferably, the dryer 22 comprises a drying introduction zone 273 for receiving fibers e.g. from fluff generator outlet 204 and for removing residual moisture from the fibers via a "flash drying" method and another drying zone 260, 262 for curing the crosslinking agent. In FIG. 1, the curing starts in zone 260 and continues through zone 262.

The FIG. 1 embodiment shows that zone 273 is coupled to the fluff generator outlet by a conduit 272 and to a source 274 of heated air, typically produced by combustion of a supply of natural gas 276 and fresh air 278. The temperature of heated air is regulated to maintain the temperature of the drying zone 273 within a range of about 200° C. to about 315° C. To achieve this temperature in zone 273, air is blown from source 274 at a temperature, for example, of about 260° C. The drying zone 273 is a J-shaped conduit that includes a necked down or reduced diameter conduit having an initial portion 273a, and a right angle portion 273b that flares to increase the diameter of the conduit as it connects with the inlet 268 of the expansion chamber defined by body 266 of drying zone 260. The reduced diameter portion increases the velocity of the flow of fibers and causes a decrease in pressure that promotes rapid evaporation and drying of the fibers. The fiber output in conduit 272 is introduced into the reduced diameter portion 273b of conduit 273 at inlet 275 immediately downstream from where portion 273a begins.

As the fiber output passes into the drying zone 273 at inlet 275, the wet fibers comprising the fiber output are substantially instantaneously exposed to the high temperature in this zone. Such rapid exposure to high temperature imparts a "flash drying" effect to the fibers, thereby causing rapid and thorough drying. Such "flash drying" also tends to separate, in a microscopically explosive manner, fibers that are touching one another, thereby ensuring thorough separation of the fibers. The passage time through the drying zone 273 is preferably less than one second, which is deliberately kept short to avoid overheating and scorching the fibers, which become highly susceptible to scorching after the residual moisture has been driven therefrom.

As the fibers enter the expanding throat of section 273b and enter first drying zone 260, pressure changes enhance the microscopic fiber explosions as water vapor is rapidly released from the fibers and pushes the fibers apart. This expanding throat 273b mates with an expanding inlet 268 to an expansion chamber defined by first drying zone 260. The FIG. 1 embodiment shows that the first drying zone 260 comprises a first tower 264 having a body portion 266, an inlet 268, and a first tower outlet 270. The dryer zone 273 is coupled via conduit 272 to the outlet of the fluff generator 190. Since the fluff generator 190 is an optional component, it is also possible to couple the dryer introduction zone 273 directly to the outlet 62 of the attrition device 32 if neither the fluff generator 190 nor the disk refiner 168 are included.

In FIG. 1, the first tower outlet 270 is shown preferably coupled via a conduit 280 to a down tube 282, which is coupled via a conduit 284 to a third conveyor fan 286 located at an inlet 288 of a second tower 290. The third conveyor fan 286 performs the function of transporting the fibers through the dryer which thereby pass through the inlet 288 of the second tower 290.

The second tower 290 is shown which includes the inlet 288, a second tower body 292, and an outlet 294 serving as an outlet of the dryer 22. Dried fibers are propelled through the inlet 288 of the second tower 290 via the third conveyor fan 286. As the fibers are lofted through the second tower body 292, they are still exposed to a curing temperature within a range of about 140° C. to about 180° C., which is sufficient to effect curing of the crosslinking agent without scorching the dry fibers. The lofting keeps the fibers separated until the crosslinking reaction is complete. The curing temperature depends upon the type of crosslinking material used to treat the fibers and also is set at a level so as not to scorch the fibers during curing. It should be noted that single stage dryers may also be used.

The dried and cured fibers exiting the dryer outlet 294 have an extremely low level of nits and virtually no knots. Further, they are not discolored from scorching and the like, and have a median fiber length substantially unchanged from the median length of the fibers comprising the mat 14.

FIG. 1 also shows a second cyclone 300 of conventional design coupled via a conduit 302 to the dryer outlet 294, serving to concentrate the fibers passing therethrough in preparation for collection. Excess air 304 is vented through the top 306 of the second cyclone 300. The resulting concentrated fibers can be collected using any of a number of collection devices 308 known in the art, such as fiber bagging devices.

EXAMPLE IX

In one specific embodiment of the invention, the fibers are moved through conduits 402, 405 at a temperature of about 250° C. First dryer 406 is approximately 50 feet tall, and has a largest diameter of 14 feet in its cylindrical upper portion. The heated fibers undergo a flash evaporation as they enter the relatively low pressure environment of large diameter tank 406. The partially dried fibers then exit through conduit 412 at a temperature of about 60° C., and are once again heated to about 250° C. by hot air from air heater 414 blowing through conduit 416. Flash evaporation of the fibers once again occurs in dryer 420, which in this example is approximately 60 feet tall and has a largest diameter of about 16 feet in its cylindrical upper portion. The flash dried fibers exit dryer 420 through outlet 424 and are collected in retention bin 428. The bin has a sufficient capacity to collect fiber output from dryer 420 for a period of 60 seconds. The retention bin is maintained at a sufficient temperature, for example 190° C. to allow the crosslinking agent to cure during the 60-second period of retention in bin 438. At the end of a 60-second retention period, the fibers are withdrawn through outlet 432 and conveyed through conduit 434 to holding tank 436.

EXAMPLE X

In this example, non-woven fibrous mats would be impregnated with a crosslinking agent, fiberized, dried, and cured using the apparatus as diagrammed schematically in FIG. 1. This example used DMDEU as a crosslinker, but any of the crosslinking agents of the present invention could be substituted for DMDEU.

Two 52-inch wide mats of southern pine kraft wood pulp fibers (type NB316 from Weyerhaeuser Company) and having a basis weight of 680 g/m$^2$ were fed to the apparatus. The mats were impregnated using dimethyloldihydroxy-ethylene urea at a concentration of about 5%, applied over both sides of each mat using a combination of spray nozzles and impregnation rollers. The loading level of crosslinking agent was about 4.5% w/w.

The treated fiber mats were fed at the rate of 8 meters/minute to the attrition device 32. The specific attrition device used in this example was equipped with six mat inlets and a rotor having 16 rows of hammers as described above around the circumference of the rotor. The rotor had a diameter of 30 inches and was rotated at an angular velocity of 1200 rpm by an electric motor. Other rpm rates have also been tested and have proven satisfactory, including extremely high rpm rates.

Random samples of fibers were obtained from the output attrition device and observed for nits. These samples were 2.6 grams and were consistently observed to have fewer than three nits on the average with most samples having no nits. The attrition device was flushed with water once every sixteen hours for cleaning purposes.

A disk refiner was employed downstream of the attrition device. This specific disk refiner was a DM36 refiner as previously mentioned.

A fluff generator as described in FIGS. 7–9 was also employed in this downstream of the disk refiner.

The temperature at the dryer input 273 in this example was within the range of 200° C. to 315° C., and conduit 273 had a diameter of 3½ feet. The tower body 266 that formed zone 260 had a diameter 7 feet, hence the diameter ratio of conduit 273 to tower 266 was 1:2. The temperature at the second tower outlet 294 was within the range of 140° C. to 180° C.

Crosslinked fiber at the output of the dryer was produced at a rate of about 5000 pounds per hour and had a nit level on an average of from 1 to 3 and a maximum bulk of greater than 22. Bulk and nit levels were determined by the following procedure, involving the production of test "handsheets" with a diameter of about 6 inches:

A "British handsheet mold" was filled with 3 to 4 inches of water. To approximately 750 mL of water were added 1.2 grams of pulp, available from Weyerhaeuser Company, followed by agitation using a Waring blender for 20 seconds to yield a pulp slurry. A 2.4 gram sample of the above obtained crosslinked fiber was added to the pulp slurry in the blender followed by agitation therein for another 10 seconds. The resulting slurry was added to the handsheet mold up to a fill mark. The slurry in the mold was gently mixed using a spatula for 3 seconds, then drained, leaving the pulp wet laid on the screen in the mold. The wet pulp layer was blotted to remove as much moisture as possible, then removed from the screen. The resulting handsheet was dried between two blotters on a drum dryer, then weighed to the nearest 0.01 gram immediately after drying.

Bulk was determined using a caliper, performed immediately after drying. Mean thickness was determined using five thickness determinations of various locations on the handsheet. Bulk was calculated in units of cm$^3$/g as follows:

$$\frac{\text{(mean thickness) cm (20.38) cm}^2}{\text{(Handsheet weight) grams}} = \text{Bulk}$$

Nit level was determined by examination of the handsheet and simple determination of the number of nits present on the handsheet. If no nits were observed a nit level of 1 was assigned to the test sheet; if 1 nit was observed, a nit level of 2 was assigned to the sheet; if 2 nits were observed, a nit level of 3 was assigned to the sheet; and so forth for higher nit levels.

Therefore, the apparatus of the present invention effectively produces a low nit level product, and one of high bulk even when crosslinking agents are used.

Definitions

As used in this specification and claims, the term "exposing cellulose fibers" to a crosslinking agent and catalyst means placing the fibers in contact with the agent and catalyst in such a way that the crosslinking reaction can occur. Examples include spraying on the fibers a solution containing a catalyst and crosslinking agent, or separately spraying the catalyst and crosslinker on the fibers at different times or places.

An aqueous solution is a solution that is more water than anything else.

A cyclic N-sulfatoimide is a ring structure containing an imide linkage

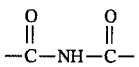

in which the H of the nitrogen is substituted with a —OSO$_3$—. Examples of a cyclic N-sulfatoimide include

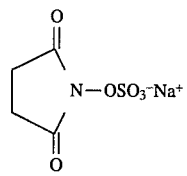

and

-continued

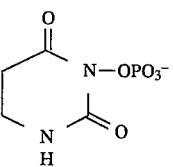

A cyclic N-phosphatoimide is a ring structure containing the imide linkage in which the H of the nitrogen is substituted with a —OPO₃—. Examples of a cyclic N-phosphatoimide include

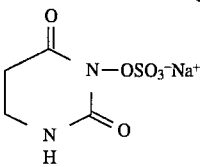

and

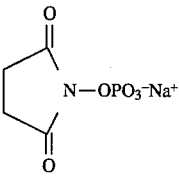

The ring structures are preferably five or six membered rings as shown above.

The term "individualizing cellulose fibers" refers to separating them in such a way that, when exposed to the crosslinking agent, primarily intrafiber bonds will form instead of interfiber bonds.

The term "conveying the mat through the fiber treatment zone and directly into a fiberizer without stopping to cure the crosslinking substance" does not exclude momentary or slight pauses. The term does specifically exclude curing periods of many hours as shown in the Chung patent discussed hereinabove.

An acid catalyst is a catalyst that reduces the pH of a reaction, while a basic catalyst increases pH. Examples of an acid catalyst include $Al_2(SO_4)_3$, $Zn(NO_3)_2$, $NH_4Cl$, HCl and $(N_4)_2HPO$. Examples of basic catalysts are $NaHCO_3$, $Na_2CO_3$, and NaOH.

Having illustrated and described the principles of the present invention in several preferred embodiment and variations thereof, it should be apparent to those skilled in the art that the invention can be modified in arrangement and detail without departing from such principles. We claim all modifications coming within the spirit and scope of the following claims.

I claim:

1. A composition of matter selected from the group consisting of (I) the sodium salt of N-sulfatosuccinimide, (II) the sodium salt of 3-sulfato-5,6-dihydrouracil, (III) the disodium salt of 2,2'-bis(N-sulfatosuccinimide), and (IV) the disodium salt of 5,5'-bis(3-sulfato-5,6-dihydrouracil) having the respective structures

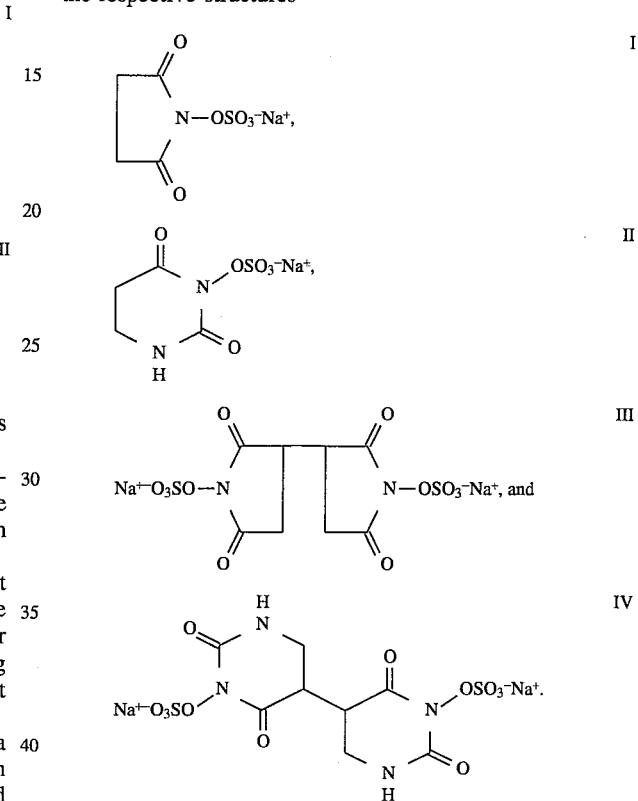

2. The composition of claim 1 selected from the group consisting of (I) the sodium salt of N-sulfatosuccinimide and (II) the sodium salt of 3-sulfato-5,6-dihydrouracil.

* * * * *

UNITED STATES PATENT AND TRADEMARK OFFICE
CERTIFICATE OF CORRECTION

PATENT NO. : 5,556,976
DATED : September 17, 1996
INVENTOR(S) : Richard A. Jewell It is certified that error appears in the above-identified patent and that said Letters Patent is hereby corrected as shown below:

ON THE TITLE PAGE add Item 73 as follows:

[73]   Assignee:   Weyerhaeuser Company
                   Tacoma, Washington

Signed and Sealed this

Seventeenth Day of June, 1997

Attest:

BRUCE LEHMAN

*Attesting Officer*        *Commissioner of Patents and Trademarks*